US012303249B2

(12) United States Patent
Shlomovitz et al.

(10) Patent No.: US 12,303,249 B2
(45) Date of Patent: May 20, 2025

(54) LOCALIZED MAGNETIC FIELD GENERATOR

(71) Applicant: ST. JUDE MEDICAL INTERNATIONAL HOLDING S.Á R.L., Luxembourg (LU)

(72) Inventors: Roie Shlomovitz, Haifa (IL); Alon Izmirli, Ganot Hadar (IL)

(73) Assignee: ST. JUDE MEDICAL INTERNATIONAL HOLDING S.Á R.L., Luxembourg (LU)

( * ) Notice: Subject to any disclaimer, the term of this patent is extended or adjusted under 35 U.S.C. 154(b) by 642 days.

(21) Appl. No.: 16/475,675

(22) PCT Filed: Jan. 5, 2018

(86) PCT No.: PCT/IB2018/050091
§ 371 (c)(1),
(2) Date: Jul. 2, 2019

(87) PCT Pub. No.: WO2018/127844
PCT Pub. Date: Jul. 12, 2018

(65) Prior Publication Data
US 2019/0343422 A1 Nov. 14, 2019

Related U.S. Application Data

(60) Provisional application No. 62/442,621, filed on Jan. 5, 2017.

(51) Int. Cl.
A61B 5/06 (2006.01)
A61B 6/00 (2024.01)
A61B 34/20 (2016.01)

(52) U.S. Cl.
CPC ............ *A61B 5/062* (2013.01); *A61B 6/4441* (2013.01); *A61B 6/547* (2013.01); *A61B 2034/2051* (2016.02); *A61B 2034/2072* (2016.02)

(58) Field of Classification Search
CPC ........... A61B 8/12; A61B 8/445; A61B 8/463; A61B 8/5215; A61B 2562/0233;
(Continued)

(56) References Cited

U.S. PATENT DOCUMENTS 6,078,177 A    6/2000  Petropoulos et al.
6,201,987 B1   3/2001  Dumoulin
(Continued)

FOREIGN PATENT DOCUMENTS

CN    101242779 B  * 12/2010  ............. G01V 3/105
DE    102012223417 A1 * 6/2014  ............. A61B 34/20
(Continued)

Primary Examiner — Sean D Mattson
Assistant Examiner — Michael Yiming Fang
(74) Attorney, Agent, or Firm — Billion & Armitage

(57) ABSTRACT

Various embodiments of the present disclosure are directed to an apparatus for generating a magnetic field for tracking of an object. The apparatus may include transmitting elements that generate a desired magnetic field (when combined) in an area of interest, and a rapid decaying magnetic field in a separate area. The separate area can be adjacent to the area of interest and can include a magnetic field-disrupting component.

13 Claims, 18 Drawing Sheets

(58) Field of Classification Search
CPC ..... A61B 1/0051; A61B 8/4494; A61B 5/062; A61B 6/4441; A61B 6/547; A61B 2034/2051; A61B 2034/2072
See application file for complete search history.

(56) References Cited

U.S. PATENT DOCUMENTS

| | | | |
|---|---|---|---|
| 6,233,476 B1 | 5/2001 | Strommer et al. | |
| 6,636,757 B1 | 10/2003 | Jascob et al. | |
| 7,197,354 B2 | 3/2007 | Sobe | |
| 7,386,339 B2 | 6/2008 | Strommer et al. | |
| 7,771,351 B1 * | 8/2010 | Talman | A61B 5/0031 600/302 |
| 10,441,236 B2 * | 10/2019 | Bar-Tal | A61B 6/02 |
| 2001/0012915 A1 | 8/2001 | Avrin et al. | |
| 2008/0287771 A1 | 11/2008 | Anderson | |
| 2009/0018434 A1 * | 1/2009 | Kimura | A61B 5/062 324/207.11 |
| 2013/0012808 A1 * | 1/2013 | Govari | G01R 33/025 439/620.21 |
| 2013/0015848 A1 | 1/2013 | Govari et al. | |
| 2013/0272592 A1 | 10/2013 | Eichler et al. | |
| 2014/0024920 A1 * | 1/2014 | Paitel | A61B 34/20 600/409 |
| 2014/0084926 A1 * | 3/2014 | Amthor | G01R 33/56 324/309 |
| 2015/0073264 A1 * | 3/2015 | Graziani | A61B 5/062 600/424 |
| 2015/0216490 A1 * | 8/2015 | Ashe | A61B 34/20 600/409 |
| 2016/0015292 A1 * | 1/2016 | Lorraine | A61B 34/20 600/424 |
| 2016/0287133 A1 | 10/2016 | Eichler et al. | |
| 2017/0135602 A1 | 5/2017 | Izmirli et al. | |

FOREIGN PATENT DOCUMENTS

| | | | | |
|---|---|---|---|---|
| EP | 0964261 A2 | * | 12/1999 | ........... G01R 33/285 |
| EP | 2546671 A1 | * | 1/2013 | ............ A61B 5/062 |
| WO | WO-2015068069 A1 | * | 5/2015 | ............ A61B 6/503 |

* cited by examiner

LOCALIZED MAGNETIC FIELD GENERATOR

CROSS-REFERENCE TO RELATED APPLICATIONS

This application claims the benefit of U.S. provisional application No. 62/442,621, filed 5 Jan. 2017, the entire disclosure of which is hereby incorporated by reference as though fully set forth herein.

This application is related to U.S. application Ser. No. 15/323,178, filed 30 Dec. 2016, which is a 371 of Patent Cooperation Treaty application no. IB2015/001675, filed 1 Jul. 2015, which claims the benefit of provisional application No. 62/098,813, filed 31 Dec. 2014, and U.S. provisional application No. 62/020,881, filed 3 Jul. 2014, the entire disclosures of which are hereby incorporated by reference as though fully set forth herein.

BACKGROUND a. Field

The instant disclosure relates to a localized magnetic field generator and related components.

b. Background Art

Medical devices, catheters, and/or cardiovascular catheters, such as electrophysiology catheters can be used in a variety of diagnostic, therapeutic, mapping and/or ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart, which can lead to a variety of symptomatic and asymptomatic ailments and even death.

A medical device can be threaded through a vasculature of a patient to a site where the diagnostic, therapeutic, mapping, and/or ablative procedure to diagnose and/or correct the condition is performed. To aid in the delivery of the medical device to the site, sensors (e.g., electrodes) can be placed on the medical device, which can receive signals that are generated proximate to the patient from a device (e.g., electromagnetic field generator). Based on the received signals, an orientation and/or position of the medical device can be computed.

BRIEF SUMMARY

Various aspects of the present disclosure are directed to apparatuses for generating a magnetic field for tracking of a target object. Such an apparatus can include a localized magnetic field generator that generates a magnetic field and controls the magnetic field in an area of interest and in a separate area, where the magnetic field in the area of interest may be independently controlled from the magnetic field in the separate area. In many embodiments, the separate area is displaced from the area of interest and includes a magnetic field-disrupting component. In various embodiments, it can be desirable to reduce the magnetic field in the separate area to mitigate the effect of the magnetic field-disrupting components on the localized magnetic field in the area of interest, which may otherwise impede the tracking accuracy of a target object in the area of interest.

In one embodiment, a magnetic field generator apparatus for tracking of an object within an area of interest is disclosed. The apparatus includes a plurality of magnetic field transmitting elements, a magnetic sensor, controller circuitry, and a signal generator. The plurality of magnetic field transmitting elements generate a magnetic field in the area of interest and a rapidly fading magnetic field in a separate area proximal the area of interest. The magnetic sensor is coupled to the object, and senses a magnetic field at the object indicative of the position of the sensor within the magnetic field. The controller circuitry is communicatively coupled to the plurality of magnetic field transmitting elements and the magnetic sensor. The controller circuitry generates an individual power generation signal for each of the plurality of magnetic field transmitting elements, and receives a signal from the magnetic sensor indicative of a position of the sensor within the generated magnetic field. The controller circuitry determines a position of the object based on the received signal from the magnetic sensor and the power generation signals to the plurality of magnetic field transmitting elements. The signal generator, communicatively coupled to the controller circuitry and the plurality of magnetic field transmitting elements, receives the individual power generation signals from the controller circuitry, and generates and transmits power to the plurality of magnetic field transmitting elements that induces the magnetic field in the area of interest and the rapidly fading magnetic field in the separate area.

In further more specific embodiments, controller circuitry adjusts the magnetic field by transmitting power generation signals to the signal generator for each of the two or more magnetic transmitting elements that increases a decay rate of the magnetic field to reduce the magnetic field in proximity to a magnetic field-disrupting object.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which.

Figure 1:
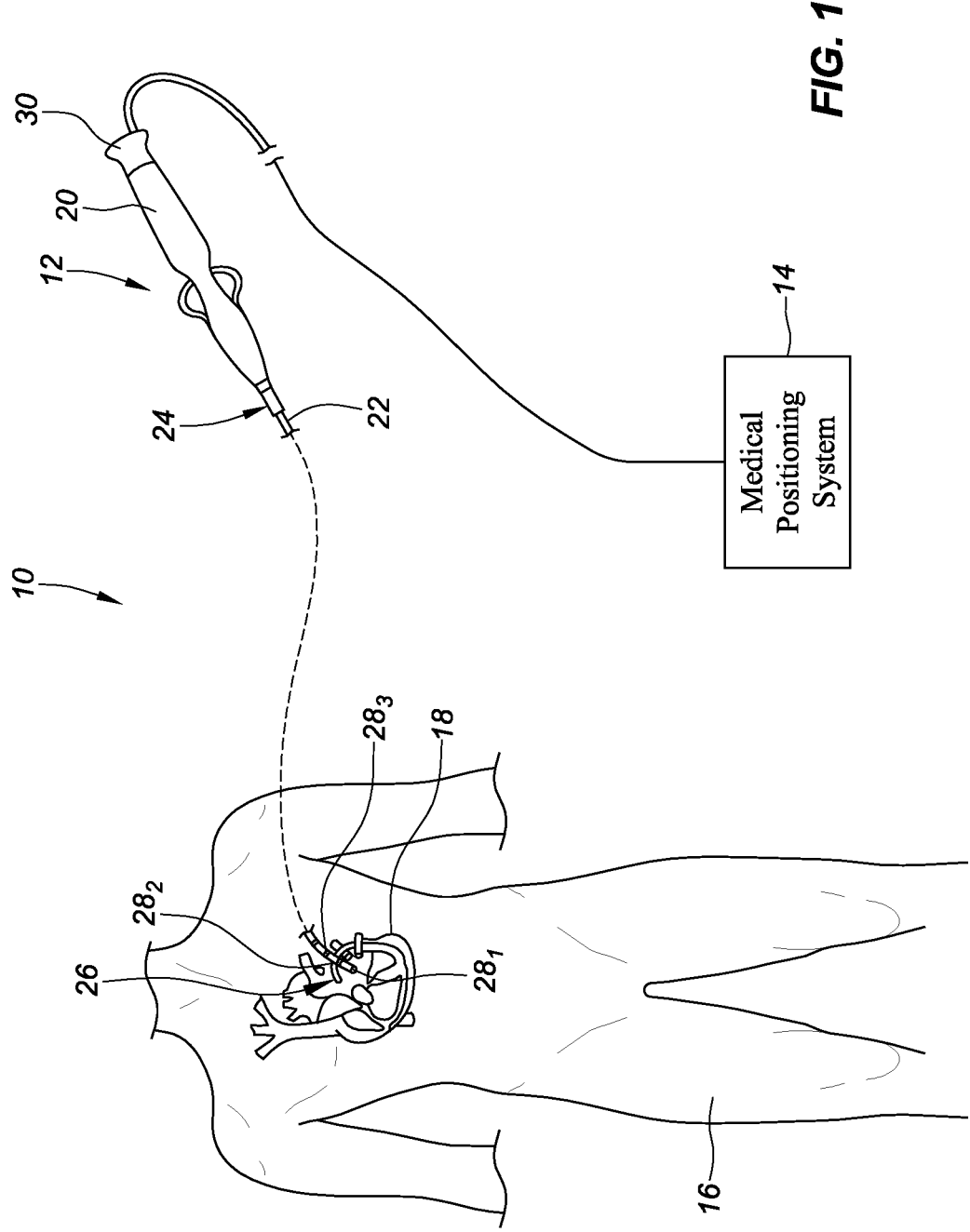
FIG. 1 depicts a systematic and diagrammatic view of an exemplary system for performing one or more diagnostic or therapeutic procedures, wherein the system includes a magnetic field-based medical positioning system, consistent with various aspects of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

Aspects of the present invention are believed to be applicable to a variety of different types of methods, devices, systems and arrangements involving generating a magnetic field for tracking of an object in an area of interest. In one example embodiment consistent with the present disclosure, a magnetic field generator for tracking of an object is disclosed. The magnetic field generator generates a magnetic field and controls the magnetic field in an area of interest and in a separate area. The separate area being displaced from the area of interest and can include a magnetic field-disrupting component. Details of the various embodiments of the present disclosure are described below with specific reference to the figures. While the present invention is not necessarily so limited to medical devices, various aspects of the invention may be appreciated through a discussion of examples using these contexts.

Various aspects of the present disclosure are directed to magnetic field transmitter configurations, pairings, and schemes that enhance a produced magnetic field in an area of interest while mitigating a magnitude or effect of the magnetic field in a separate area. In one example, a localized magnetic field is generated and used in order to track the location of an electromagnetic sensor (e.g., within a catheter). However, where ferrous objects are located in proximity to the magnetic field transmitters, the localized magnetic field can be distorted and as a result the predicted position of the electromagnetic sensor can be erroneous. This can happen even if the distorting objects are far from the area of interest (for example, opposite the area of interest relative to the transmitters). The source of the distortion in the magnetic field may include phenomena where an object is responding to the magnetic field by creating its own magnetic field. A few examples of such phenomenon include the formation of eddy currents in a conductive material, and paramagnetism/diamagnetism that are represented by the magnetic permeability constant of the material. These magnetic distortions increase with the strength of the magnetic field in the vicinity of the distorting object(s), and often the mass and ferrous/conductive material density of the distorting object. As a result, aspects of the present disclosure are directed to reducing the strength of the magnetic field in the separate area (including, e.g., the ferrous object) relative to the magnetic field in the area of interest, which thereby reduces the magnetic distortions produced within the magnetic field (in proximity to the area of interest). In reference to the present application, ferrous objects are referred to herein as including any object that creates a distortion in a magnetic field, including, for example, ferrous objects, metallic (conductive) objects, and any other object that otherwise affects the accuracy of a magnetic tracking system—such as eddy current or magnetic field producing objects.

Some aspects of the present disclosure are directed to (re)directing the orientation of a magnetic field in such a way as to mitigate a magnetic field distorting effect of a ferrous object in proximity to an area of interest. Importantly, by determining a magnetic field orientation relative to the area of interest and distorting object, and re-directing the orientation of a produced magnetic field, a weaker distortion in the area of interest can be attained.

In the present disclosure, methods, apparatuses, and systems are disclosed for achieving a fast fading magnetic field. In the fast fading magnetic field, the magnetic field distorting objects can be in the same magnetic orientation/direction/vicinity as an area of interest, without causing significant magnetic interference (by way of eddy currents)—which would otherwise impede the localization of a target within the area of interest. In one embodiment consistent herewith, an array of transmitting coils (also referred to as a matrix) is disclosed, the combination, phase, driving current, and/or polarity of which alone (or in combination) produce a magnetic field that decays faster than a magnetic field produced by a single magnetic field transmitting coil. This magnetic coil array enables the production of a stronger magnetic field close to the magnetic coil transmitters (where the area of interest is located), while reducing the magnetic field strength further away from the transmitters (out of the area of interest) at low/negligible values.

Other uses for magnetic field transmission using a plurality of transmission coils, having opposite phase and/or polarity, is to cancel the magnetic field in the vicinity of the distorting object by transmitting with a second coil from the other side of the distorting object. Also, the application of several magnetic field transmitting coils can change the orientation of the magnetic field in the vicinity of the distorting object; which may reduce the resulting eddy current produced by the distorting object as the change in orientation reduces the strength of the magnetic field at the distorting object—where the magnetic poles of the distorting object and the produced magnetic fields align.

Aspects of the present disclosure are implemented in order to achieve precise localization of an object within a magnetic field, where the magnetic field-based measurement is conducted in an environment that lacks shielding from other magnetic impetuses. Specifically, various applications of the present disclosure may be utilized in hospital rooms, including surgical suites, where the magnetic localization system can operate in an environment including large pieces of ferrous capital equipment (e.g. fluoroscopy C-arm, lights, operating table, instruments, etc.). Also, many of these ferrous/conductive (magnetic distorting) objects are not static, but may dynamically move about the room during the operation, constantly changing the distorting eddy currents affecting the magnetic field produced by the magnetic localization system. Distortion of the magnetic field during localization of an object therein deteriorates the accuracy of the target object localization within the magnetic field. Accordingly, aspects of the present disclosure are directed to reducing the magnetic distortion produced by ferrous objects outside an area of interest for localization, thereby improving the repeatability and accuracy of the localization system in response to environments with static and/or dynamic ferrous objects in proximity to the area of interest.

FIG. 1 depicts a diagrammatic view of an example system 10 for performing one or more diagnostic or therapeutic procedures, wherein the system comprises a magnetic field-based medical positioning system 14, consistent with various aspects of the present disclosure.

In some embodiments, and with reference to FIG. 1, the system 10 can include a medical device 12 and a medical positioning system 14. The medical device 12 can include an elongated medical device such as, for example, a catheter or a sheath. For purposes of illustration and clarity, the description below will be limited to an embodiment wherein the medical device 12 comprises a catheter (e.g., catheter 12). It will be appreciated, however, that the present disclosure is not meant to be limited to such an embodiment, but rather in other example embodiments, the medical device may comprise other medical devices, such as, for example and without limitation, sheaths, guidewires and the like. In yet further embodiments, the medical device 12 may be any medical device wherein real-time location-based data may be advantageous to a procedure in which it is used.

With continued reference to FIG. 1, distal tip 26 of catheter 12 can be inserted into a patient's body 16, and more particularly, into the patient's heart 18. The catheter 12 may include a handle 20, a shaft 22 having a proximal end portion 24 and a distal end portion 26, and one or more sensors 28 mounted in or on the shaft 22 of the catheter 12. As used herein, "sensor 28" or "sensors 28" may refer to one or more sensors $28_1$, $28_2$, . . . $28_N$, as appropriate and as generally depicted. In an exemplary embodiment, the sensors 28 are disposed at the distal end portion 26 of the shaft 22. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

The shaft 22 can be an elongated, tubular, flexible member for movement within the body 16. The shaft 22 supports, for example and without limitation, sensors and/or electrodes mounted thereon, such as, for example, the sensors 28, associated conductors, and possibly additional electronics used for signal processing and conditioning. The shaft 22 may also permit transport, delivery, and/or removal of fluids (including irrigation fluids, cryogenic ablation fluids, and bodily fluids), medicines, and/or surgical tools or instruments. The shaft 22 may be made from conventional materials such as polyurethane, and define one or more lumens configured to house and/or transport electrical conductors, fluids, or surgical tools. The shaft 22 may be introduced into a blood vessel or other structure within the body 16 through a conventional introducer. The shaft 22 may then be steered or guided through the body 16 to a desired location, such as the heart 18, using means well known in the art.

The sensors 28 mounted in or on the shaft 22 of the catheter 12 may be provided for a variety of diagnostic and therapeutic purposes including, for example and without limitation, electrophysiological studies, pacing, cardiac mapping, and ablation. In an example embodiment, one or more of the sensors 28 are provided to perform a location or position sensing function. More particularly, and as described in greater detail below, one or more of the sensors 28 can be a positioning sensor that provides information relating to the location (e.g., position and orientation) of the catheter 12, and the distal end portion 26 of the shaft 22 thereof, in particular, at certain points in time. Accordingly, in such an embodiment, as the catheter 12 is moved along a surface of a structure of interest of the heart 18 and/or about the interior of the structure, the sensor(s) 28 can be used to collect location data points that correspond to the surface of, and/or other locations within, the structure of interest. These location data points can then be used for a number of purposes such as, for example and without limitation, the construction of surface models of the structure of interest. For purposes of clarity and illustration, the description below will be with respect to an embodiment wherein a single sensor 28 of the catheter 12 comprises a positioning sensor. It will be appreciated, however, that in other example embodiments, which remain within the spirit and scope of the present disclosure, the catheter 12 may comprise more than one positioning sensor as well as other sensors or electrodes configured to perform other diagnostic and/or therapeutic functions, for example to find the six degrees of freedom of the catheter. As will be described in greater detail below, the sensor 28 can include a pair of leads extending from a sensing element thereof (e.g., a coil) that electrically couple the sensor 28 to other components of the system 10, such as, for example, the medical positioning system 14.

Figure 2:
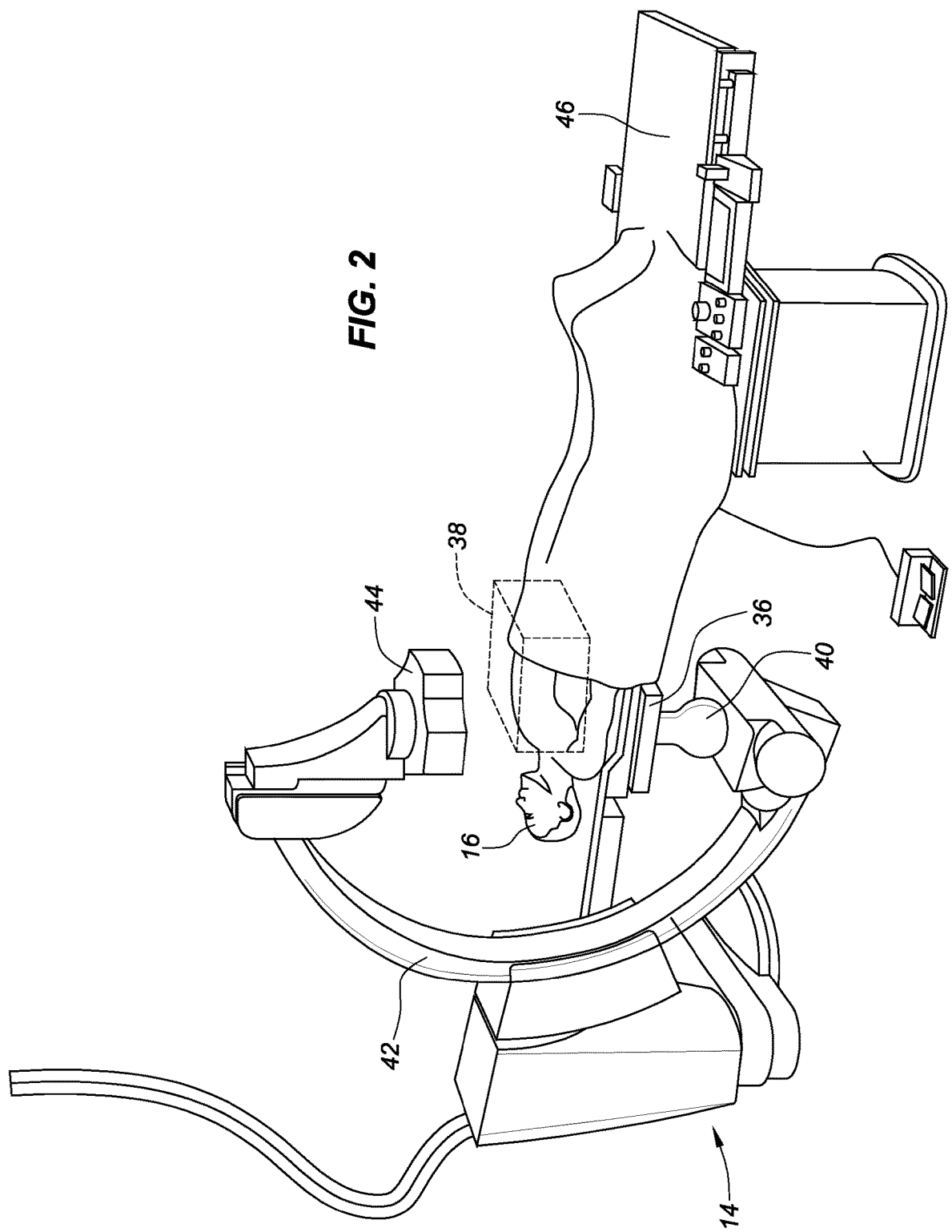
FIG. 2 depicts an isometric side-view of a medical positioning system, consistent with various aspects of the present disclosure.

With reference to FIGS. 1 and 2, the medical positioning system 14 will now be described. The medical positioning system 14 can be provided for determining a position and/or orientation of the sensor 28 of the catheter 12, and thus, the position and/or orientation of a distal portion of the catheter 12. In some embodiments, the medical positioning system 14 may comprise a magnetic field-based system such as, for example, the MediGuide™ system from MediGuide Ltd. (now owned by St. Jude Medical, Inc.), and as generally shown with reference to one or more of U.S. Pat. Nos. 6,233,476; 7,197,354; and 7,386,339, the entire disclosures of which are incorporated herein by reference.

In some embodiments, and in general terms, the medical positioning system 14 comprises, at least in part, a magnetic field generator 36 for generating a magnetic field for tracking of an object (e.g., a distal portion of catheter 12). The magnetic field generator 36 can generate a low-strength magnetic field(s) in and around the patient's chest cavity (e.g., an area of interest during a cardiac surgical procedure), which can be defined as a three-dimensional space designating an area of interest 38, as shown in FIG. 2. In such an embodiment, and as briefly described above, the catheter 12 includes a positioning sensor 28 comprising a magnetic sensor that detects one or more characteristics of the low-strength magnetic field(s) applied by the magnetic field generator 36 when the sensor 28 is disposed within the area of interest 38. The sensor 28, which in an example embodiment comprises a magnetic coil, can be electrically/communicatively coupled with processing circuitry of a medical positioning system. The signals received by the processing circuitry corresponds to the sensed characteristics of the magnetic field(s) to which the magnetic coil is exposed. The processing circuitry, responsive to the detected signal, calculates a three-dimensional position and/or orientation for the sensor 28 and an input to the magnetic field generator 36. Thus, the medical positioning system 14 enables real-time tracking of each magnetic sensor 28 of the catheter 12 in three-dimensional space, and thereby, real-time tracking of the catheter 12.

As shown in FIG. 2, the magnetic field generator 36 can be located underneath a patient examination table 46, between an x-ray source 40 and the patient examination table 46. For example, the magnetic field generator 36 can be coupled to the patient examination table 46. In some embodiments, as discussed herein, the magnetic field generator 36 can be a mobile device, which can be placed on a chest of the patient and used to generate the magnetic field for tracking of the object. In yet other embodiments, aspects of the present disclosure can be directed to a magnetic field generator 36 which includes one or more sensors on various sides of an area of interest 38 of a patient 16. In such an embodiment, magnetic field distortions within (and external to) the area of interest may be cancelled by, for example, producing opposing magnetic fields on opposite sides of a distorting object, and thereby cancelling a magnetic field at the location of the distorting object. In yet other embodiments, magnetic field transmitters may be positioned at various locations around the area of interest 38 to create varying magnetic field orientations that reduce an eddy from the distorting object.

Aspects of the present disclosure address challenges associated with generating a magnetic field for tracking an object, where the magnetic field is disrupted as a result of ferrous/conductive objects that are located proximate to a magnetic field and/or a magnetic field generator 36 that produces the magnetic field. For example, magnetic field-disrupting objects can be any ferrous/conductive object located proximal to a magnetic field generator 36, including x-ray source 40, portions of the patient examination table 46, c-arm 42, x-ray image intensifier 44 associated with the medical positioning system 14, and/or any other ferrous/conductive object of sufficient ferrous content to affect the magnetic field given the distance from the field. In some cases, even ferrous/conductive objects that are located far away from the magnetic field generator and/or the magnetic field produced by the magnetic field generator can cause disruptions to the magnetic field. Even small ferrous objects may form a considerable disruption to the magnetic field located within the area of interest 38. This can be problematic, because each magnetic sensor of the catheter is reliant on a consistent (e.g., undisrupted) magnetic field to determine a position and/or orientation of the sensor and/or catheter.

In various embodiments of the present disclosure, a catheter may include, one or more magnetic sensors. The catheter may also include electrode sensors which function in conjunction with an impedance based tracking system.

In one example, a source of the disturbance to the magnetic field can be an eddy current effect and/or a change in the magnetic field caused by materials with high permeability (e.g., ferrous objects) in the surrounding of an area of interest 38. In various other examples, the magnetic field disrupting components can include magnetically conductive and/or magnetically permeable objects located within a proximity to the magnetic field generator 36 and/or a magnetic field produced by the magnetic field generator 36. As used herein, magnetically permeable is a material property indicating a material's ability to support the formation of a magnetic field therein. Magnetically conductive is a material property indicative of the material's disinclination to support a formation of a magnetic field therein. For example, a magnetically permeable material can bend magnetic field lines toward the material, while a magnetically conductive material can bend magnetic field lines away from the material. Accordingly, aspects of the present disclosure are directed to preventing magnetic distortions in proximity to a magnetic localization system associated with materials that are magnetically permeable and/or conductive.

In some examples, where the magnetic field-disrupting object is stationary, an eddy current caused by the magnetic field-disrupting component can be factored out when determining a location of the catheter 12, as its static position is readily detected over time and compensated therefore. However, in a medical positioning system 14, such as that depicted in FIG. 2, the x-ray source 40, the c-arm 42, the x-ray image intensifier 44, as well as the patient examination table 46 can all move with respect to the magnetic field generator 36 and can cause varying disturbances to the magnetic field produced by the magnetic field generator 36, which can be unpredictable. As such, eddy currents produced by the magnetic field-disrupting components can constantly vary and can be difficult to factor out.

In some example embodiments, a magnetic field generator 36 may be coupled to c-arm 42, allowing for the movement of the magnetic field relative to the patient examination table 46 and the patient 16.

In one example embodiment, the medical positioning system 14 may further include an impedance-based system for determination of a position and/or orientation of a catheter. However, in some previous approaches, the impedance-based system can suffer from a shift and/or drift of the coordinates determined through the impedance-based system. In addition, a distorted representation of a geometry of the heart can be generated when using an impedance based system. For instance, electrical currents used in an impedance based system can travel three-dimensionally along a path of least resistance. As such, part of the electrical currents can leave a transverse plane with blood flow, for example, through an impedance transfer—which can result in a distorted representation of the geometry of the heart. When the impedance based system is used in conjunction with a magnetic tracking system, as disclosed herein, the problems of the impedance based system disclosed above may be corrected for.

In embodiments as disclosed above, eddy currents in the conductive material can be reduced and/or eliminated entirely by reducing the magnetic field strength produced by the magnetic field generator 36 in the vicinity of a magnetic field distorting object. Due to the accuracy of the magnetic tracking system, the magnetic tracking system may be used to correct for the shift and/or drift associated with coordinates determined through the impedance-based system. Further, some embodiments of the present disclosure are directed to a magnetic field-based system that may adjust the decay rate of a magnetic field produced by the magnetic field generator 36. As such, embodiments of the present disclosure can be configured to increase a ratio of a magnetic field strength located in an area of interest (that includes an object being tracked with the magnetic field) versus a magnetic field strength located in a separate area that includes a distorting object(s).

In one example embodiment consistent with various aspects of the present disclosure, a magnetic field generator 36 produces a decaying magnetic field and positioned proximate to an area of interest 38, such that a size of a magnetic field produced outside the area of interest 38 by the magnetic field generator 36 is reduced; the decaying magnetic field reduces the chance of magnetic field disturbance within the area of interest by ferrous/conductive objects outside the area of interest 38.

In some approaches, an eddy current caused by a ferrous object (e.g., a c-arm 42), in proximity to an area of interest 38, can be factored out when determining a location of the catheter 12. Specifically, the medical positioning system 14 may be calibrated in order to account for the effect on the magnetic field within an area of interest 38 due to a ferrous object(s) in proximity to the area of interest. For example, the disturbance caused to the magnetic field via the eddy currents can be factored out when determining a position of an object located in an area of interest; however, such calibration techniques are only effective for static ferrous objects (e.g., large capital equipment within the operating suite). Alternatively, or combined with such calibration techniques, embodiments of the present disclosure can avoid creation of eddy currents due to ferrous objects altogether, thereby avoiding the need for calibrating a medical positioning system to compensate for such magnetic distortions. Such embodiments may reduce installation time and decrease installation complexity.

Figure 3:
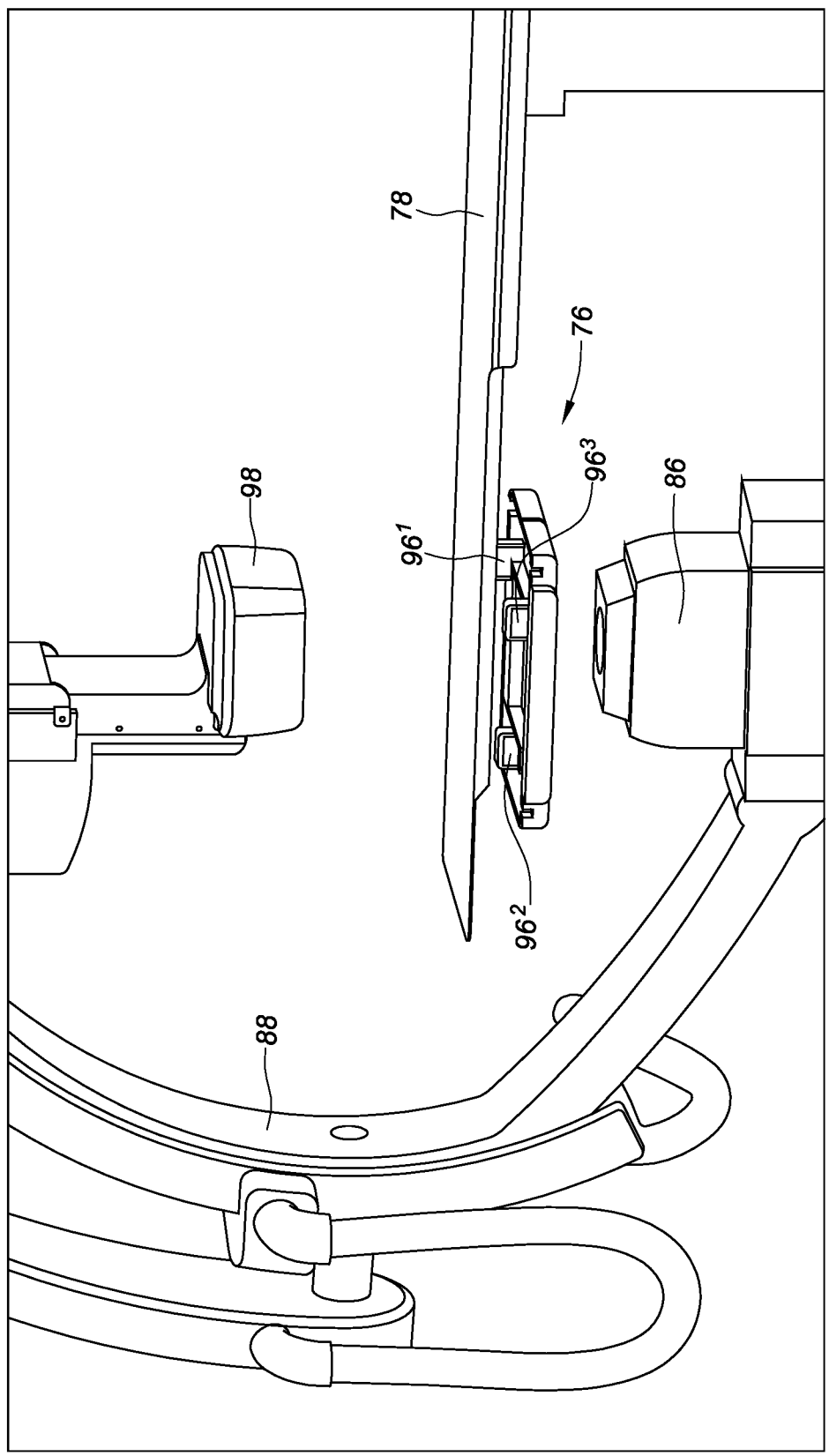
FIG. 3 depicts a close-up isometric side-view of the medical positioning system in FIG. 2, consistent with various aspects of the present disclosure.

FIG. 3 depicts a close-up isometric view of the medical positioning system of FIG. 2, consistent with various aspects of the present disclosure. As discussed herein, the medical positioning system can include a localized magnetic field generator 76. The localized magnetic field generator 76 can be located between a patient examination table 78 and a magnetic field-disrupting component (e.g., x-ray source 86, c-arm 88). The localized magnetic field generator 76 can include a plurality of magnetic transmitting elements $96^{1-3}$. In some embodiments, the plurality of magnetic transmitting elements $96^{1-3}$ can be located beneath patient examination table 78. In yet other embodiments, the plurality of magnetic transmitting elements $96^{1-3}$ can be located anywhere within the operating suite, so long as the plurality of magnetic transmitting elements $96^{1-3}$ are in close proximity to an area of interest 38 (as shown in FIG. 2).

In various embodiments of the present disclosure, magnetic transmitting elements $96^{1-3}$ of localized magnetic field generator 76 may be positioned in such a way as to create a clear path along a vertical axis through an area of interest 38, such that x-rays from the x-ray source 86 can pass between the magnetic transmitting elements, through the patient examination table 78, to the image intensifier 98 without picking up metallic objects associated with the magnetic transmitting elements that may obscure areas of interest within the patient.

In some embodiments, as discussed herein, the magnetic transmitting elements $96^{1-3}$ can be mounted in different locations relative to a path of x-rays from the x-ray source 86 to the image intensifier 98. For example, the magnetic transmitting elements $96^{1-3}$ can be mounted around the path. In some embodiments, the magnetic transmitting elements $96^{1-3}$ can be mounted with different orientations with respect to the x-ray path. For example, the magnetic transmitting elements $96^{1-3}$ can be mounted at an angle with respect to the x-ray path. In some embodiments, the magnetic transmitting elements $96^{1-3}$ can direct a magnetic field towards a particular point. In one example, the particular point can be inside the area of interest 38 (as shown in FIG. 2). In addition, the magnetic transmitting elements $96^{1-3}$ can be rotated with respect to one another. For instance, the magnetic transmitting elements $96^{11}$ can be similarly oriented with respect to one another, such that they are aligned with an x-ray path.

In various embodiments consistent with the present disclosure, magnetic transmitting elements $96^{1-3}$ can be split center transmitters and can be communicatively coupled to a magnetic field generator in such a way as to create an array of magnetic transmitting elements with magnetic field outputs that are synchronized. In further embodiments, the magnetic transmitting elements $96^{1-3}$ can operate independently, and in parallel to one another (e.g., where a magnetic field emitted from adjacent magnetic transmitting elements have opposing magnetic field directions, and/or opposite transmission direction). In applications where precise control of an area of interest is desirable, aspects of the present disclosure are directed to positioning all of the magnetic transmitting elements to a single focal point in space. The super positioning behavior of each of the magnetic transmitting elements may be utilized to direct the magnetic field in a manner that creates a destructive interference at the location of the distorting object. By super positioning the magnetic transmitting elements toward the magnetic distortion object, the magnetic field generated by the various magnetic transmitting elements repel (or otherwise cancel one another out) around the distortion object creating an area substantially magnetic field free. As a result, the magnetic distortion object may not introduce eddy currents into the magnetic field that negatively impacts localization of a target object within the area of interest—as there are no magnetic fields in proximity to the distortion object to propagate the eddy currents.

In operation, localized magnetic field generator 76 includes a plurality of magnetic transmitting elements $96^{1-3}$ can produce a low-power magnetic field that envelops an area of interest 38 (as shown in FIG. 2) within the patient (on a patient examination table 78) without significantly extending the field beyond such areas, where ferrous objects within the operating suite can create eddy currents that extend back into the area of interest. As discussed in more detail below, various aspects of the present disclosure are directed toward operating the plurality of magnetic transmitting elements $96^{1-3}$ in opposing current states (e.g., polarities), to assist in the rapid decay of the produced magnetic field in areas outside the area of interest. The resulting magnetic field produces lower-strength magnetic fields (or diminishes the existence of magnetic fields entirely) proximal ferrous objects (outside the area of interest) that would otherwise create eddy currents which can manipulate the field lines of the magnetic field. The faster the decay of the magnetic field outside the area of interest, the weaker the magnetic field at the ferrous object. As discussed above, the resulting eddy current caused within a magnetic field by a ferrous object is relative to the strength of the field at the ferrous object. Accordingly, where the field strength at a ferrous object can be decreased (by rapidly decaying the field), the eddy current has a reduced effect has on an area of interest where magnetic localization is desired.

Figure 4:
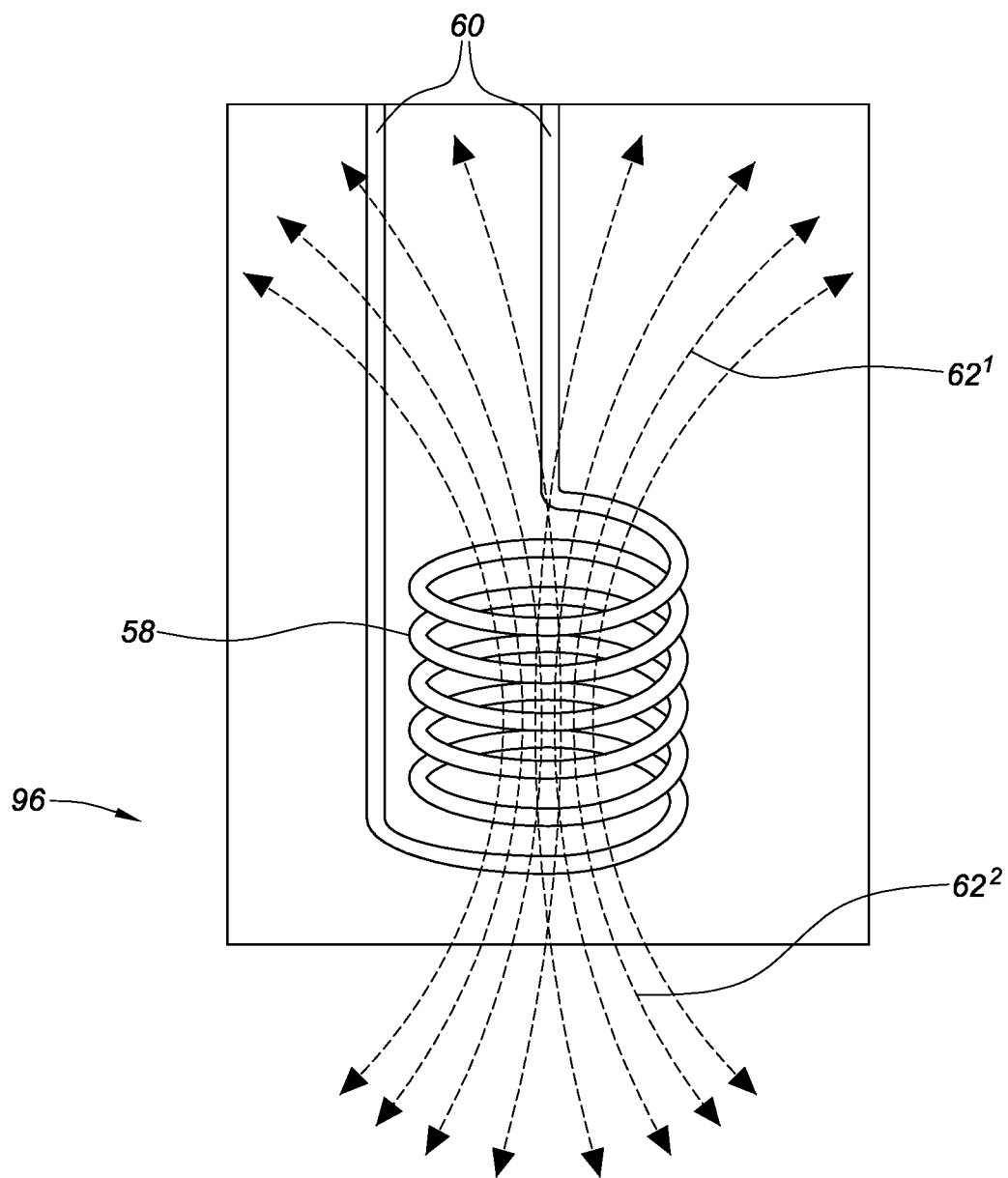
FIG. 4 depicts a front view of a magnetic transmitting element of a magnetic field generator, consistent with various aspects of the present disclosure.

FIG. 4 depicts a magnetic transmitting element 96 of a magnetic field generator 36 (as shown in FIG. 2) for generating a magnetic field for tracking of an object, consistent with various aspects of the present disclosure. The magnetic field generator may include one or more magnetic transmitting elements 96 that together produced a desired magnetic field. The magnetic transmitting element 96 can include a coil 58, which can be energized via leads 60 to produce a magnetic field $62^{1-2}$ that extends through a center of the coil 58 and out a top bottom of the coil 58. In one example, magnetic field lines $62^1$ extend from a top of the coil 58 and magnetic field lines $62^2$ extend from a bottom of the coil 58. As discussed herein, in some previous approaches, magnetic field lines extending from a magnetic field generator used to produce a magnetic field for tracking of an object could be affected by magnetic field-disrupting components, such as a c-arm, x-ray source, etc. In some examples, disturbances (e.g., eddy currents) can be created in the magnetic field $62^{1-2}$ and cause inaccuracies in the tracking of an object within the field.

In some embodiments of the present disclosure, magnetic transmitting element 96 of a magnetic field generator can generate the magnetic field $62^{1-2}$ and control the magnetic field $62^{1-2}$ in an area of interest and in a separate area. For example, magnetic transmitting element 96 can operate in conjunction with other magnetic transmitting elements within the magnetic field generator to vary the strength, decay rate, and orientation of the produced magnetic field. The area of interest can include the object (e.g., catheter), while the separate area can be displaced from the area of interest and can include a magnetic field-disrupting component (e.g., ferrous object). For example, as depicted in FIG. 2, the separate area can include a x-ray source 40, the c-arm 42, or another object that can disturb the magnetic field produced by the magnetic field generator.

In one example embodiment, coil 58 can create magnetic fields $62^{1-2}$ via a flow of electrical current through the coil, and a change to the current driving the coil can control the produced magnetic fields $62^{1-2}$. For example, a reduced current through the coil results in a reduced strength in magnetic fields $62^{1-2}$. Similarly an increased current through the coil results in an increased strength in magnetic fields $62^{12}$. As discussed in more detail below, when used in conjunction with other coils, coil 58 and a paired coil(s) may be driven with opposite currents to create magnetic fields that exhibit increased field decay, or a current variation between the two or more coils may re-direct an orientation of the magnetic field. As yet another example, when driven together, the two or more coils may produce an amplified magnetic field.

In some embodiments, the coil 58 can be formed of various thicknesses of wire and various numbers of windings. In some examples, as a wire thickness and the number of windings changes, a range and/or strength of the magnetic field can change. As such, the numbers of windings of the coil 58 can be chosen to create a magnetic field $62^{1-2}$ that is sized such that little to no disturbance of the magnetic field $62^{1-2}$ is caused by the magnetic field-disrupting components. A thickness of the wire can typically vary from 3 millimeters to 10 micrometers. However, the thickness of the wire can be greater than 3 millimeters or less than 10 micrometers, in some embodiments.

Figure 5A:
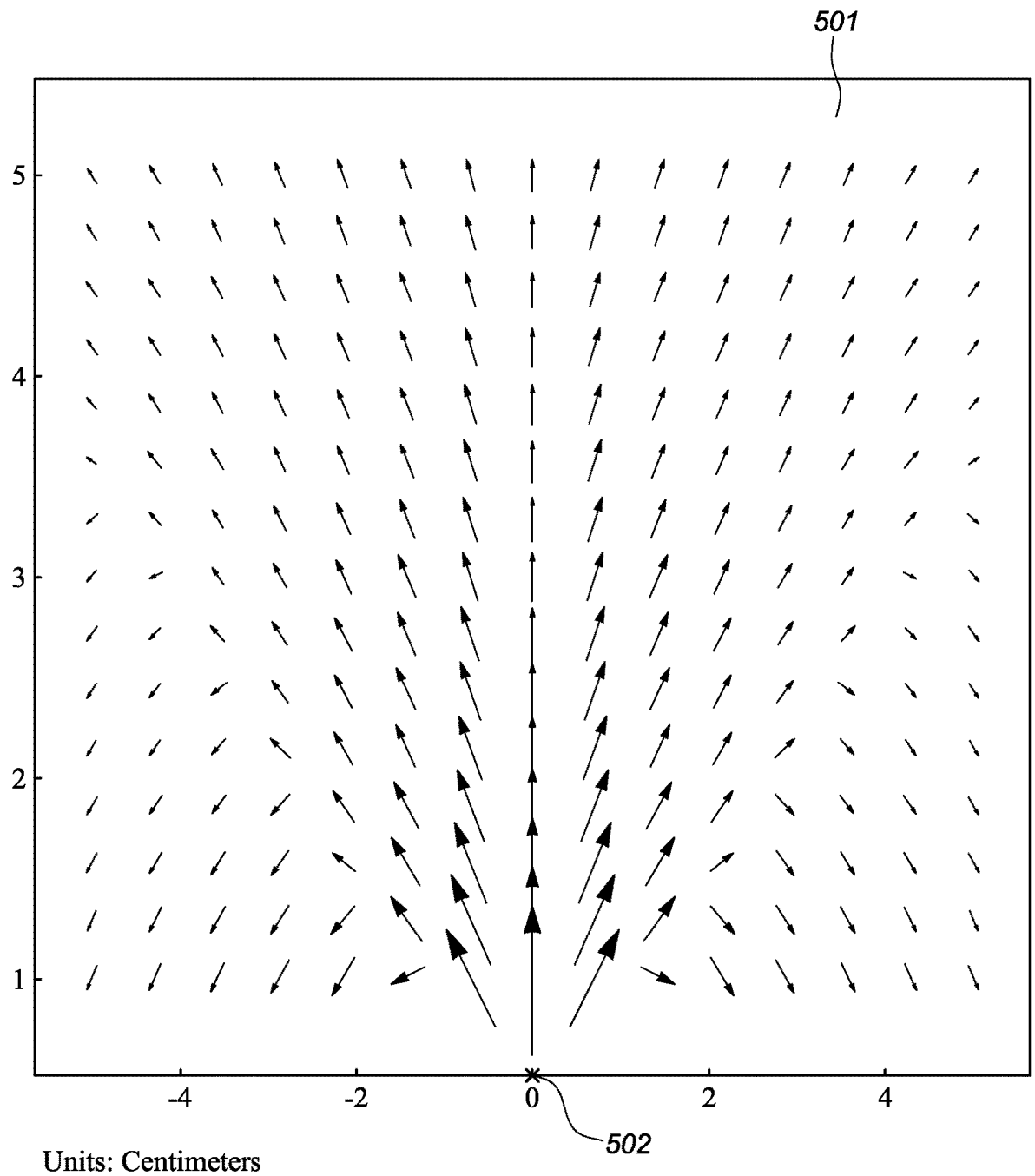
FIG. 5A PRIOR ART depicts magnetic field lines produced by a PRIOR ART magnetic field generator.

FIG. 5A PRIOR ART depicts magnetic field lines 501 of a single coil 502 generating a magnetic field, with the arrow length indicative of a relative strength of the field at a location, and the direction of the arrow indicative of the orientation of the field at the location. As shown in FIG. 5A, the single coil magnetic field transmitter produces a magnetic field that decays slowly—for example $1/r^3$ where r is the distance from the coil.

Figure 5B:
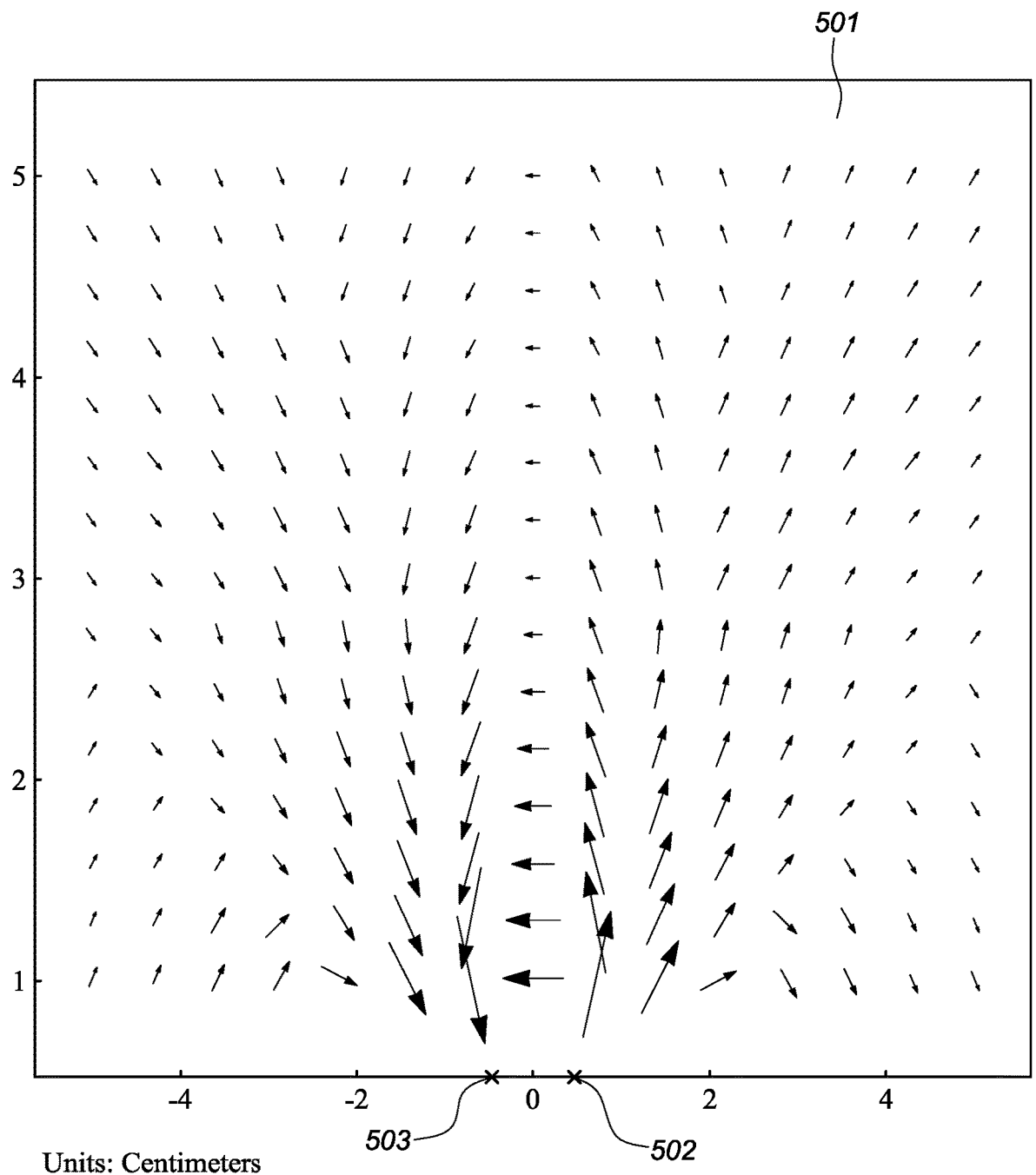
FIG. 5B depicts magnetic field lines produced by a magnetic field generator, consistent with various aspects of the present disclosure.

FIG. 5B depicts magnetic field lines 501 transmitted by a dual coil configuration (with the two coils located at 502 and 503, respectively) of a magnetic field generator, with the arrow length indicative of a relative strength of the field at a location, and the direction of the arrow indicative of the orientation of the field at the location. As shown in FIG. 5B, the dual coil array (when the coils are driven by opposite currents) produces a magnetic field that exhibits enhanced field decay, as compared to PRIOR ART FIG. 5A. By using such a dual coil array configuration (as shown in, for example, FIGS. 7A and 7B) to produce a magnetic field, a field may be produced in an area of interest for magnetic localization of a target object, while quickly diminishing the strength of the magnetic field outside the area of interest to limit the production of eddy currents which may impact the magnetic field within the area of interest.

In another implementation of a dual coil array, varying current and polarity through each of the coils can shape the magnetic field orientation. Importantly, such magnetic field orientation shaping can be used in the vicinity of a known distorting object. For example, in the case of a distorting object that lacks spherical symmetry (e.g., varying material density and/or composition, and varying geometry), the misalignment between the lines of the magnetic field and the surface of the distorting object can result in increased eddy current propagation; specifically, the misalignment results in an increased error rate in the localization of a target object within the magnetic field at least because the eddy current has a greater effect on the generated magnetic field lines. Even in the case of a small sphere (as the distorting object), the change to the magnetic field within the area of interest can be significant enough to distort the resulting estimated position of a target object (especially where the localization system estimation requires a high degree of precision and repeatability). This phenomenon is due to a dipole magnetic field having varying field strengths depending on the relation of the location and the orientation of the dipole source. For example, as shown in FIG. 5B, the dual coil array configuration does not only exhibit a varying decay rate compared to FIG. 5A, but also a different field line orientation in space (at a number of locations within the magnetic field).

Figure 6A:
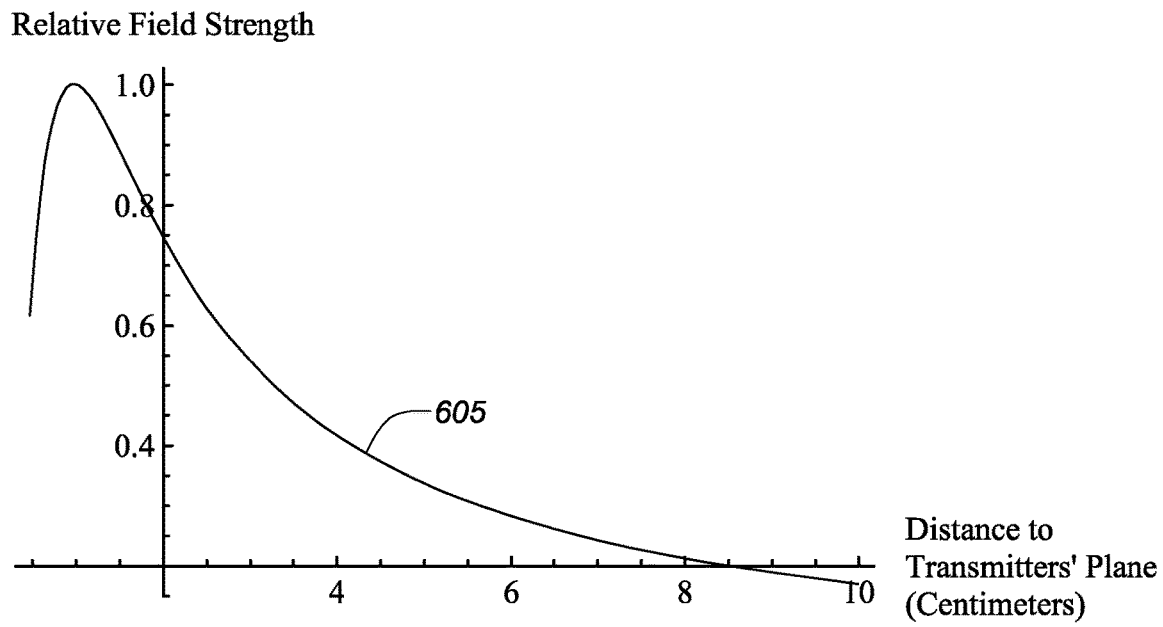
FIG. 6A depicts relative magnetic field strength of a magnetic field produced by a magnetic field generator, consistent with various aspects of the present disclosure.

FIG. 6A plots a line 605 which is a relative magnetic field strength as a function of the distance from the plane of the coils. In the present embodiment, a magnetic field generator includes two magnetic field transmitters (e.g., coils) spaced 1 centimeter apart and operating with opposing polarity to one another. In the present embodiment, the magnetic field generator has a driving current calibrated so that the ratio of the magnitude of the magnetic field at a distance associated with an area of interest is 1. This ratio rapidly decreases as the distance from the area of interest increases.

Figure 6B:
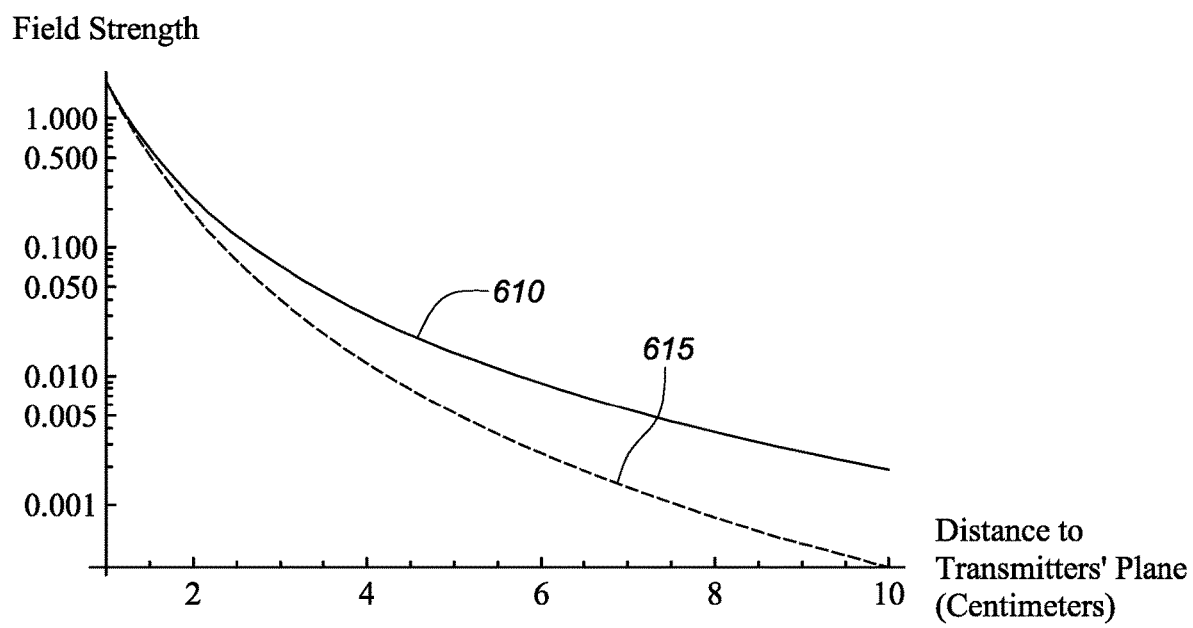
FIG. 6B depicts magnetic field strength of a magnetic field produced by a magnetic field generator, consistent with various aspects of the present disclosure; and that of a PRIOR ART magnetic field generator.

In FIG. 6B, line 615 plots strength of a magnetic field produced by a magnetic field generator, including a dual coil magnetic field transmitter array, as a function of distance from the transmitters, consistent with various aspects of the present disclosure. Line 610 plots the reduction in strength of a magnetic field from a single coil magnetic field transmitter as a function of distance from the transmitter. As can be seen in FIG. 6B, the magnitude of the magnetic field in the dual coil transmitter array 615 decays more quickly as a product of distance than the single coil configuration 610. As a result, ferrous objects outside of an area of interest, but within the distances plotted in FIG. 6B (for example) would produce reduced eddy currents in response to the magnetic field produced by the dual coil array (as opposed to the single coil magnetic field transmitter), at least because the ferrous object would be exposed to a reduced magnetic field strength.

Figure 6C:
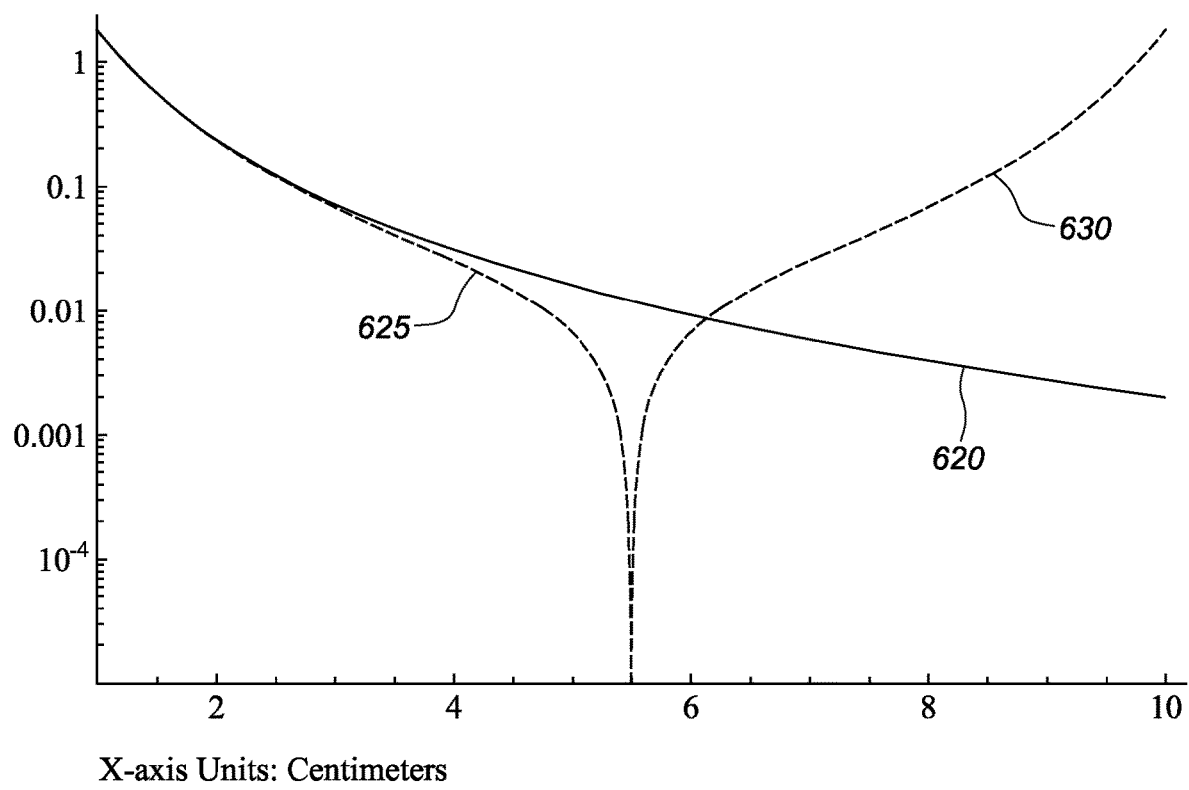
FIG. 6C depicts magnetic field strength of a magnetic field produced by a magnetic field generator consistent with various aspects of the present disclosure, and that of a PRIOR ART magnetic field generator.

In FIG. 6C, line 620 plots a magnetic field strength of a single coil magnetic field transmitter located at position 0 centimeters ("c.m.") as the field extends to position 10 c.m. Lines 625 and 630 plot a magnetic field strength of a dual coil array magnetic field generator, wherein the magnetic coils are located opposite from one another. Specifically, one of the coils of the dual coil array at position 0 c.m. and the other at position 10 c.m., with both coils being driven with a current of equal and opposite polarity. As a result of the opposite polarity produced by each of the coils, the magnetic field is cancelled out in an area approximately between the two coils (e.g., position ~5.5 c.m.).

In one embodiment, the cancellation effect of the opposing magnetic fields may be directed in the vicinity of the distorting object. In such an embodiment, the driven-current and polarity of each of the magnetic coils can be adjusted to position a low strength or no magnetic field around the distorting object. Similarly, embodiments including three or more magnetic coils may be implemented to achieve magnetic field cancellation areas. In various further embodiments, the current driving the two or more magnetic coils may be adjusted in order to direct an orientation of the generated magnetic field in such a way as to align the orientation of the magnetic field near the distorting object to be parallel to the surface of the distorting object to minimize the effect of the distorting object on the generated magnetic field. This may be particularly beneficial where the distorting object lies outside of an area where complete magnetic field cancellation can be achieved, or where the distorting object lies in close proximity to a target object.

Figure 7A:
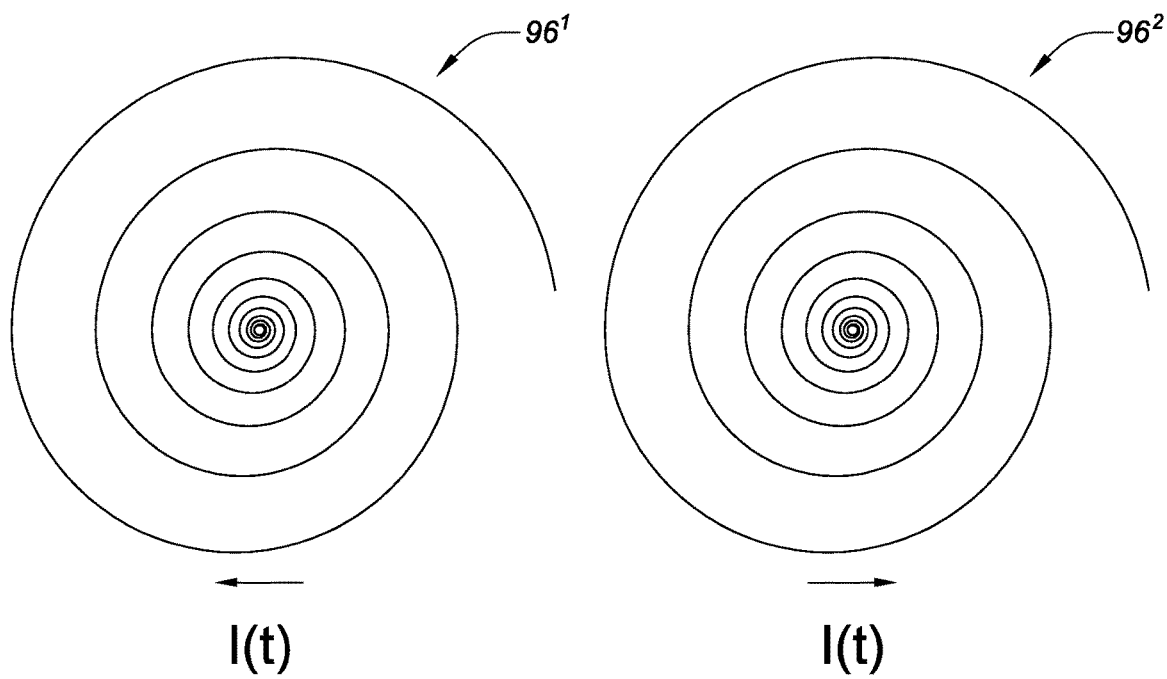
FIGS. 7A and 7B depict diagrammatic views of magnetic field generators for tracking of an object, consistent with various aspects of the present disclosure.
Figure 7B:
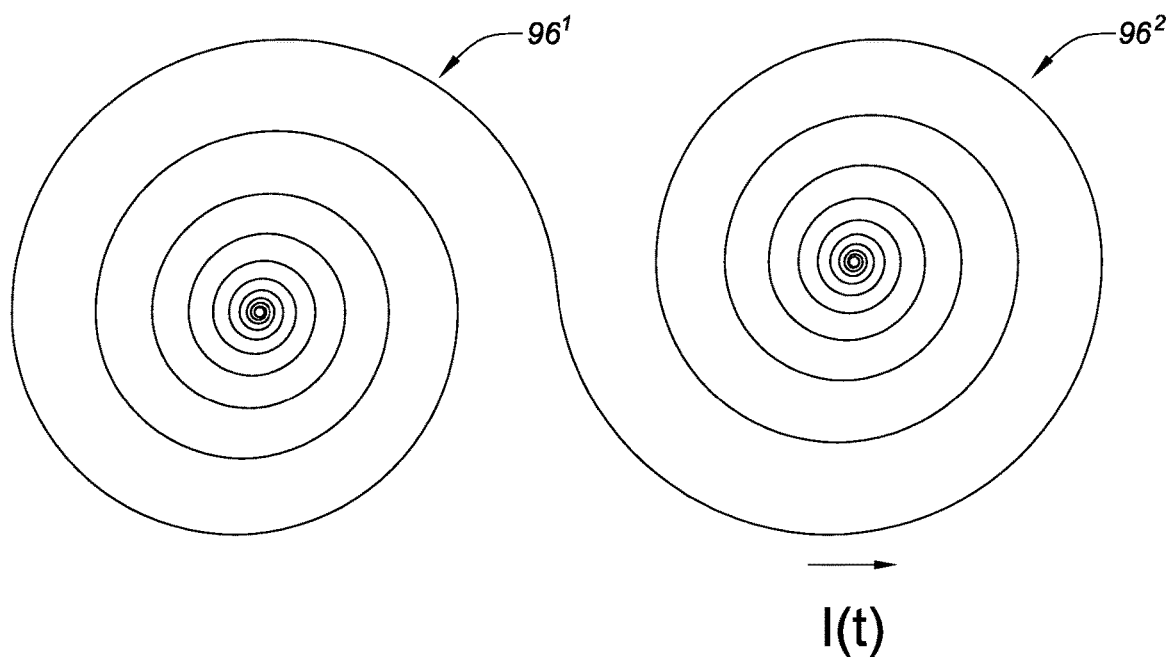

FIGS. 7A and 7B depict representations of magnetic field generators including two magnetic field transmitters 96' and $96^2$ for generating a magnetic field for tracking of a target object, consistent with various aspects of the present disclosure. It is to be understood that the representations of the magnetic field generators would not necessarily reflect the actual shape of the magnetic field transmitters. That is, the magnetic field transmitters would not necessarily be planar. Instead, the magnetic field transmitters may be similar to the magnetic field transmitters shown in FIG. 4, for example, with the coils being wound longitudinally around an air core. Further examples of magnetic field transmitters are disclosed in U.S. Patent Publication 2016/0287133, the entirety of which is hereby incorporated by reference as though fully set forth herein. It is also to be understood that the representations of the magnetic field generators in FIGS. 7A and 7B would require appropriate wiring to electrically couple the magnetic field generators to signal generator circuitry, for example.

As shown in FIG. 7A, the two magnetic field transmitters 96' and $96^2$ are configured side-by-side, each with coils that wind counter-clockwise from an exterior to an interior of a spiral. In the magnetic field transmitter 96', a current is driven from an interior of the spiral to an exterior of the spiral. In the magnetic field transmitter $96^2$, the current is driven opposite from magnetic field transmitter 96', from an exterior to an interior of the spiral. As a result, each of the magnetic field transmitters 96' and $96^2$ generate magnetic fields (in response to the flow of current through the coils) of opposite polarity. That is the magnetic field transmitter 96' produces a magnetic field that extends into a plane defined by the coil, and the magnetic field of the magnetic field transmitter $96^2$ extends out of the same plane.

It has been discovered that the magnetic field emitted from a single coil transmitter decays in accordance with $(1/r)^{\wedge}3$ where r is the distance from the coil. In various aspects of the present disclosure, using multi-coil systems, such as shown in FIGS. 7A and 7B, a transmitted magnetic field decays faster than a single coil configuration, and thereby produces a magnetic field with a decreased magnitude outside an area of interest (e.g., further away from the magnetic field transmitters). For example, by using two identical coils as shown in FIG. 7A, the first with a current $I(t)=\cos(wt)$ and the other with an opposite current, $I(t)=-\cos(wt)$, a magnetic field can be produced with a field that decays at a rate, e.g., $(1/r)^{\wedge}4$ where $2\pi w$ is the alternating current frequency and t is time.

To get the same effect as the magnetic field generator shown in FIG. 7A, a single wire coil wound around one center in a given direction and then wound around a second center in the same way but in an opposite direction is disclosed in FIG. 7B. Magnetic field transmitters $96^1$ and $96^2$ produce a magnetic field that decays faster than a single coil configuration, and thereby produces a magnetic field with a decreased magnitude outside an area of interest. The magnetic field generator arrays of FIGS. 7A and 7B, including magnetic field transmitters $96^1$ and $96^2$, both produce quadruple distribution far from the coils, compared to dipole distribution of a single coil magnetic field transmitter configuration.

Figure 8:
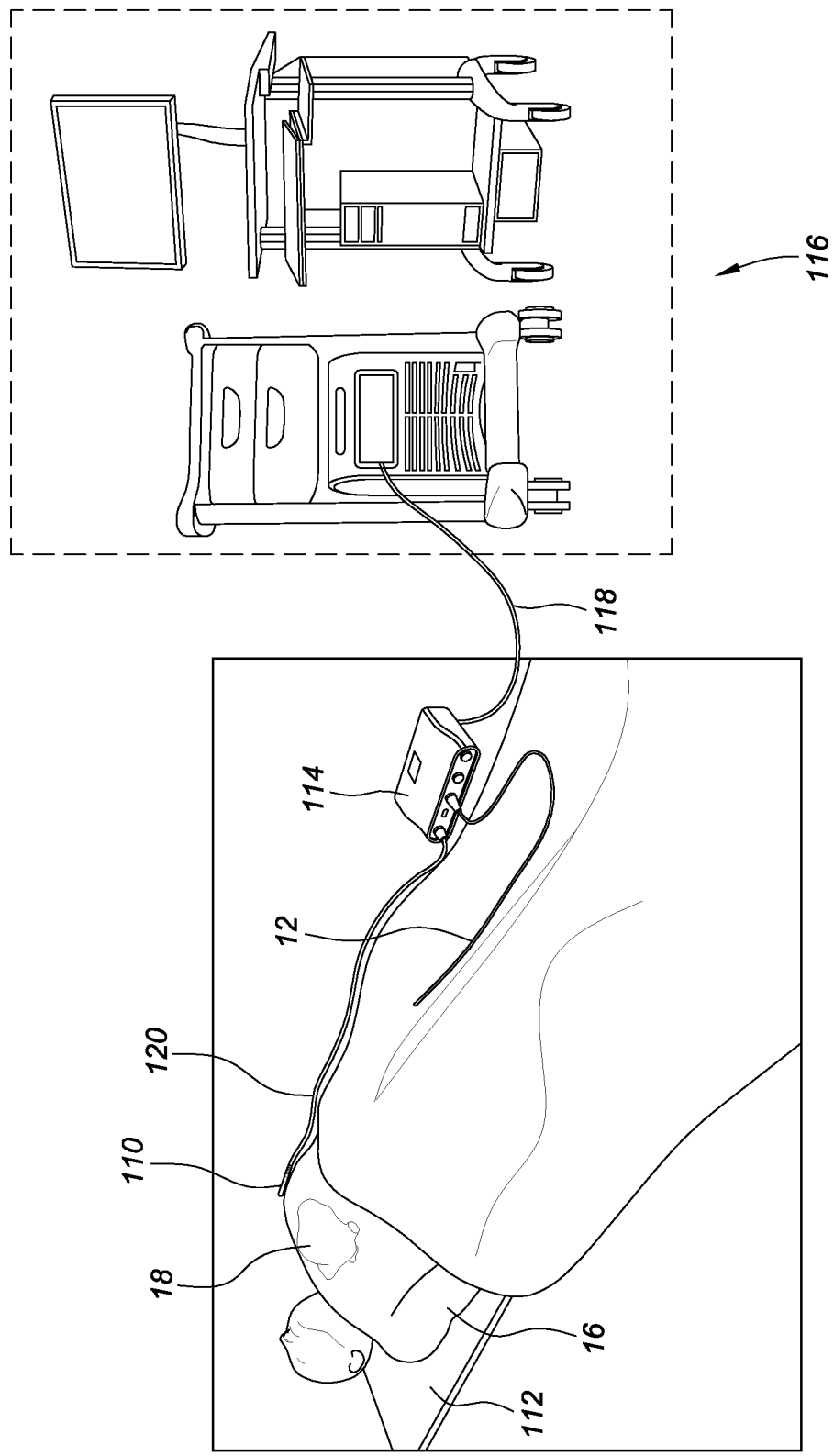
FIG. 8 depicts an isometric front view of a mobile medical positioning system, consistent with various aspects of the present disclosure.

FIG. 8 depicts a mobile medical positioning system 116, consistent with various aspects of the present disclosure. The mobile medical positioning system 116 can include a mobile localized magnetic field generator 110 that can be placed proximate to a heart 18 of the patient 16. Such an embodiment may be utilized where, for example, a catheter 12 is conducting diagnostics and/or therapy within a patient's heart 18, and localization of the catheter's 12 position within the heart 18 is desirable. In such an embodiment, the mobile localized magnetic field generator 110 can be placed on a chest of the patient 16, on a side of the patient, on a back of the patient, etc. In one specific example, where it is desirable to place the mobile localized magnetic field generator 110 near a back-side of the patient 16, the mobile localized magnetic field generator 110 can be placed between the patient examination table 112 and the patient 16.

The mobile medical positioning system 116 can generate a magnetic field and control the magnetic field in an area of interest and can control the magnetic field in a separate area. In some embodiments, as discussed herein, the area of interest can include an object (e.g., catheter 12), which can be inserted into the patient's heart 18. The separate area can be displaced from the area of interest 38 (as shown in FIG. 2) and can include a magnetic field-disrupting component. For example, the separate area can include an x-ray source, c-arm, or other ferrous object(s) that can disturb the magnetic field produced by the mobile localized magnetic field generator 110.

In some embodiments, mobile localized magnetic field generator 110 can generate a localized magnetic field in the area of interest, which can be detected by a sensor included at a distal portion of catheter 12. The mobile localized magnetic field generator 110 can be coupled to a controller 114 via a cable 120, which can provide power to the mobile localized magnetic field generator 110 and can control the magnetic field generated by the mobile localized magnetic field generator 110. The sensor can be configured to detect one or more characteristics of the magnetic field, which can be used to determine a three-dimensional position and/or orientation for the sensor.

In various embodiments, the sensor can be coupled to a controller 114 via a sensor cable, the sensor providing electrical signals to the controller 114 for determination of the three-dimensional position and/or orientation of the sensor (and the catheter 12). The controller 114 can further be coupled via a cable 118 to a mobile medical positioning system 116 to provide the position and/or orientation data for the sensor. The mobile medical positioning system can process the electrical signals received from the controller 114 to determine the three-dimensional position and/or orientation or to simply receive position and/or orientation data where the controller 114 processes the signals received from the sensor to determine the position and/or orientation. In some embodiments, the mobile medical positioning system 116 may overlay such position and orientation data for the sensor over a Magnetic Resonance Image, an x-ray image, or other image-type data such as ultrasound to facilitate the clinician's understanding of the location of the catheter 12 within the patient's heart 18. In some embodiments, the cable 118 can have magnetic shielding around a core of the cable to prevent interference from magnetic field-disrupting components. In yet other embodiments, the sensor within the catheter 12 may include wireless transceiver circuitry to facilitate non-wired communication of position and orientation data of the catheter 12 to the controller 114.

Some embodiments of the present disclosure can be compatible with cardiac mapping systems such as, for example, Ensite Velocity™ cardiac mapping system. In some examples, the mobile localized magnetic field generator 110 can be coupled to the cardiac mapping system via cables 118, 120, and the controller 114.

Figure 9:
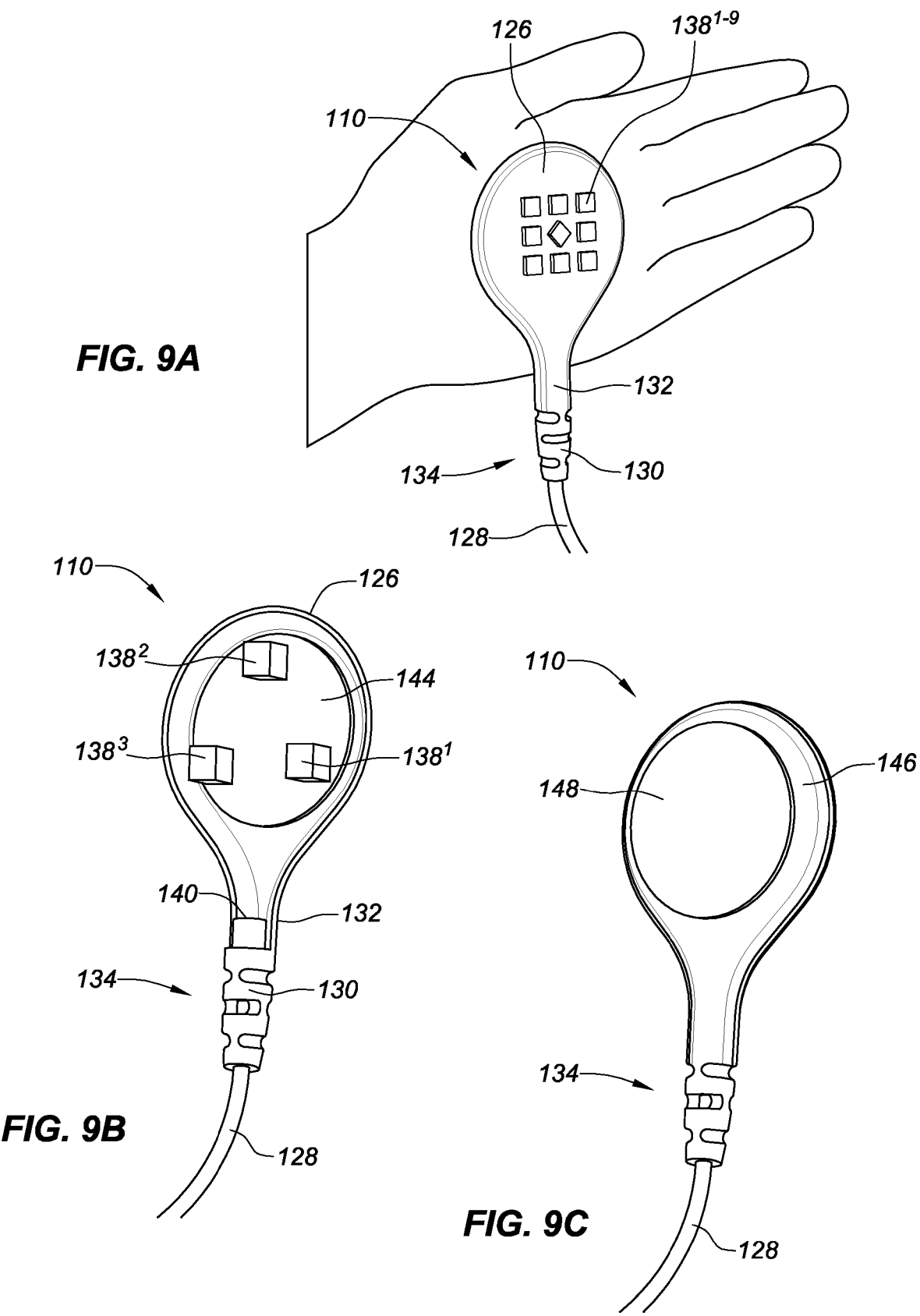
FIG. 9A depicts an isometric back view of a mobile, localized magnetic field generator, consistent with various aspects of the present disclosure.
FIG. 9B depicts a partial cross-sectional front view of the mobile, localized magnetic field generator of FIG. 9A, consistent with various aspects of the present disclosure.
FIG. 9C depicts a front view of the mobile, localized magnetic field generator of FIG. 9A, consistent with various aspects of the present disclosure.

FIG. 9A depicts a back view of a mobile localized magnetic field generator 110, consistent with various aspects of the present disclosure. The mobile localized magnetic field generator 110 can include a back plate 126. The back plate 126 can be directed away from an area of interest when the mobile localized magnetic field generator 110 is positioned proximate to the area of interest. In various embodiments consistent with the present disclosure, the magnetic field generator 110 may include two or more magnetic transmitting elements $138^{1-N}$. In the present embodiment, the magnetic field generator 110 includes nine magnetic transmitting elements $138^{1-9}$. The magnetic transmitting elements $138^{1-9}$ can control the magnetic field in the area of interest and a separate area. In one example implementation of the magnetic field generator 110, the magnetic transmitting elements $138^{1-9}$ can be driven in such a way as to direct a magnetic field generated by the transmitting elements toward the area of interest and/or away from the separate area that can include magnetic field-disrupting components. Further specific implementations of a magnetic field generator 110 including nine transmitting elements is discussed in relation to FIG. 12.

The mobile localized magnetic field generator 110 can include a wire mount portion 134, that can be configured for connecting a wire 128 with the mobile localized magnetic field generator 110. In some embodiments, the wire mount portion 134 can include a rigid portion 132 and a flexible portion 130. The flexible portion 130 can prevent the wire 128 from flexing at one point, thus increasing a distance over which the wire bends and reducing a chance that the wire 128 will fray or break. In some embodiments, the rigid portion 132 can be used to hold and/or position the mobile localized magnetic field generator 110. In some embodiments, the back plate 126, the rigid portion 132, and the flexible portion 130 can be formed from a single piece of material. Alternatively, the back plate 126, the rigid portion 132, and/or the flexible portion 130 can be formed from separate pieces of material and can be connected with one another.

FIG. 9B depicts an internal front view of the mobile localized magnetic field generator 110, consistent with various aspects of the present disclosure. In the present example, a front plate has been removed from the mobile localized magnetic field generator 110. The mobile localized magnetic field generator 110 can be tear drop shaped in some embodiments, as depicted in FIGS. 9A-C. However, the mobile localized magnetic field generator 110 can be formed as a square, triangle, rectangle, etc. In yet other embodiments consistent with the present disclosure, the magnetic field generator 110 need not be a mobile-type system, but instead may be mounted to a c-arm, an operating table, or other fixed capital equipment within the operating suite. In such embodiments, the magnetic field generator 110 may be adjustable to allow for various patient sizes and to create a magnetic field in an area of interest on the patient (e.g., heart, lungs, etc.). While mobile implementations may benefit from reduced magnetic distortions associated with ferrous objects in close proximity to a periphery of a patient's body, fixed-type magnetic field generators may be more precise as the field generator location would not be subject to patient movements (e.g., breathing, and other body adjustments).

FIG. 9B depicts a partial cross-sectional front view of a simplified magnetic field generator 110, with only three magnetic transmitting elements $138^{1-3}$. In the present embodiment, the magnetic transmitting elements $138^{1-3}$ are communicatively coupled to a circuit board 144 including electronic circuity that provides power to the magnetic transmitting elements. The circuit board 144 may be coupled to a back plate 126. In some embodiments, the circuit board 144 can be a triangular, square, rectangular, circular disc, etc. The magnetic transmitting elements $138^{1-3}$ can be of a small size(e.g., smaller coils). In some embodiments, the magnetic transmitting elements $138^{1-3}$ can generate a relatively smaller magnetic field, as the mobile localized magnetic field generator 110 can be placed directly on a patient 16 creating a smaller distance between the transmitting elements and one or more magnetic sensors connected to a distal end of a catheter shaft within a patient. As such, because the mobile localized magnetic field generator 110 is located closer to the one or more sensors, a magnetic field with a lesser strength can be utilized, while still allowing for the one or more magnetic sensors to detect characteristics of the magnetic field. In addition, use of the magnetic field with the lesser strength can be beneficial because the magnetic field of lesser strength may interact with the magnetic field-disrupting components (e.g., ferrous objects in magnetic proximity to the mobile localized magnetic field generator 110) to a lesser extent. For example, while the mobile localized magnetic field generator 110 can provide a magnetic field that is of a sufficient strength within the area of interest, the magnetic field may be of a strength in the separate area such that it does not interact with magnetic field-disrupting components.

In some embodiments, a wire mount portion 134 includes a cable 128 that extends into flexible portion 130 and/or rigid portion 132. The rigid portion 132 can contain an opening 140 through which wires included in the cable 128 can pass. The wires can provide power to each of the magnetic transmitting elements $138^{1-3}$ from a controller 114 at a proximal end of the cable 128.

In some embodiments of the present disclosure, the magnetic field produced by the magnetic transmitting elements $138^{1-3}$ can be further shaped through use of a plurality of synchronized magnetic transmitting. In an example, a plurality of synchronized transmitting elements can be grouped together and act as a single transmitting element (e.g., transmitting element $138^1$) and produce a magnetic field at a same frequency. Additional transmitting elements can be grouped together and act as different magnetic transmitting elements that produce a second, third, etc. magnetic field at different frequencies with respect to the single transmitting element and with respect to one another. As such, a synchronized magnetic field transmission can be produced to shape the magnetic field, increase/decrease the rate of spatial degradation of the magnetic field, and/or (re-)orient magnetic field lines. In some embodiments, a Halbach array, and/or a Helmholtz coil can be used to shape the magnetic field produced by the magnetic transmitting elements.

FIG. 9C depicts a front view of a mobile localized magnetic field generator 110, consistent with various aspects of the present disclosure. The mobile localized magnetic field generator can include the wire mount portion 134 for connection of wire 128. The mobile localized magnetic field generator 110 can include a front plate 146. The front plate 146 can connect with the back plate via an adhesive and/or mechanical fastener. In some embodiments, magnetic transmitting elements can be enclosed by the back plate 126 and the front plate 146.

The front plate 146 can include a pad 148, which can be a same or similar size and/or shape as the mobile localized magnetic field generator 110. The pad 148 can be connected with the front plate 146 and can be located between a patient 16 and the mobile localized magnetic field generator 110. In some examples, the mobile localized magnetic field generator 110 can include the pad 148 to improve fit and comfort of the mobile localized magnetic field generator 110 on a patient 16. Alternatively, and/or in addition, the pad 148 can improve a conductive coupling between the mobile localized magnetic field generator 110 and the patient's body. For example, a contact gel (e.g., conductive gel) can be placed between the pad 148 and the patient 16 to improve the flow of a magnetic field produced by the mobile localized magnetic field generator 110 to the sensor within the patient.

The pad 148 can be formed from a non-conductive material, in some embodiments. By forming the pad from a non-conductive material, interference with the magnetic field produced by the mobile localized magnetic field generator 110 can be avoided.

In some embodiments, the size of mobile localized magnetic field generator 110 can allow for minimal interference to an x-ray image and/or minimal occlusion of an x-ray image taken of a patient. For example, an x-ray image taken of the patient may not be obscured by the mobile localized magnetic field generator 110, since a small percentage of x-rays passing through a patient 16 interact with the mobile localized magnetic field generator 110, due to its small size. In yet other embodiments, where the magnetic field generator is secured to an operating room table, the location of the various magnetic transmitting elements situated around the patient may be positioned in such a way as to minimize obscuring an x-ray image. In yet further embodiments, the magnetic field generator may be retractable in order to move the various magnetic transmitting elements out of an x-ray image frame.

Figure 10:
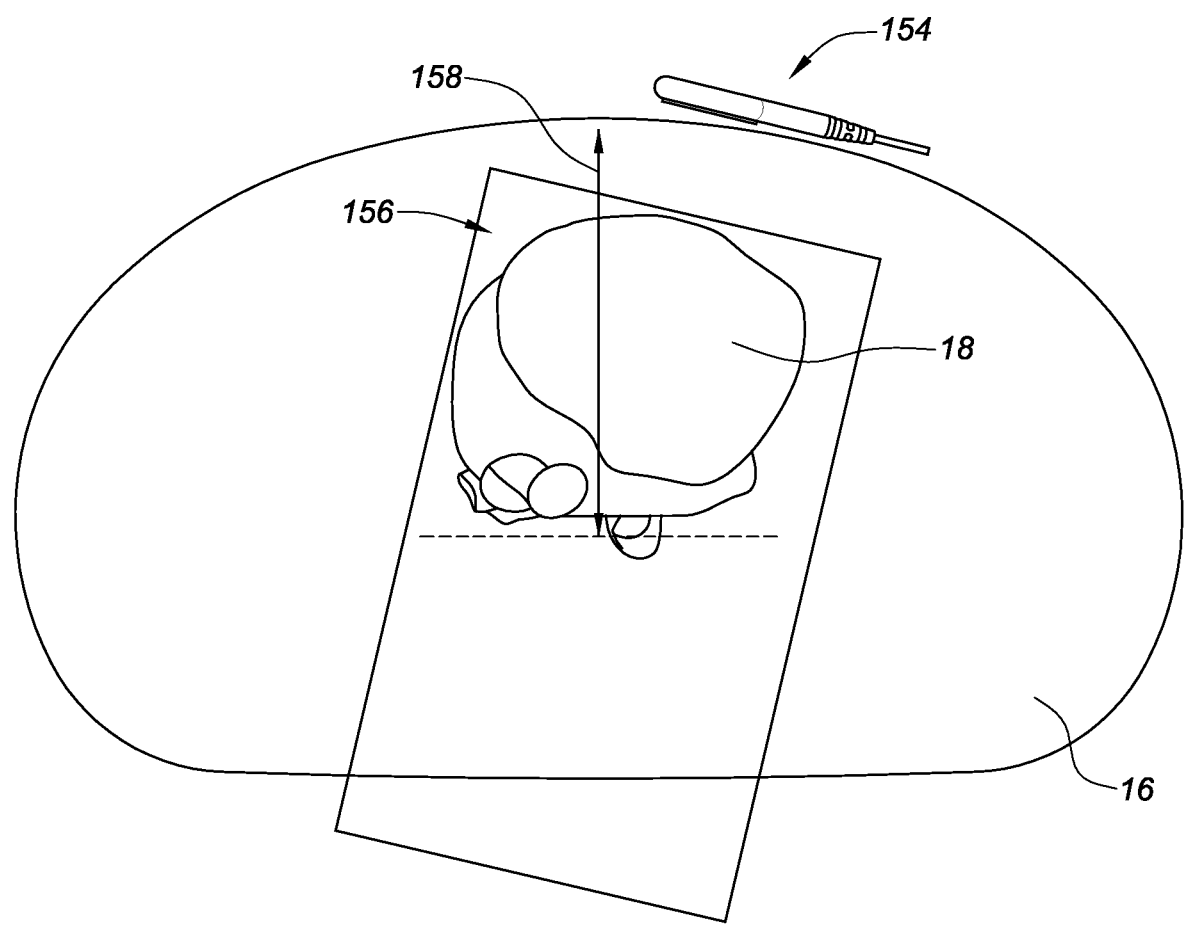
FIG. 10 depicts a motion box generated by a mobile, localized magnetic field generator placed on a patient's chest, consistent with various aspects of the present disclosure.

FIG. 10 depicts a motion box 156 generated by a mobile localized magnetic field generator 154 placed on a chest of a patient 16, consistent with various aspects of the present disclosure. In such an example embodiment, the patient's heart 18 (area of interest) is located a distance away from the mobile localized magnetic field generator 154. The mobile localized magnetic field generator 154 can create a magnetic field that defines the motion box 156, where movement of sensors associated with a catheter can be monitored. In one example embodiment, the motion box 156 can encompass the heart 18. In some embodiments, it can be desirable to have a motion box 156 that is inclusive of the heart 18, and exclusive of a separate area that includes magnetic field-disrupting components. As such, the mobile localized magnetic field generator 154 can be designed accordingly. For instance, where the localized magnetic field generator 154 is placed on the chest, a particular size of coil can be used in the mobile localized magnetic field generator 154, and/or a particular amount of current can be driven through the one or more coils to create a magnetic field that substantially encompasses the heart 18. A dimension of the magnetic field generator 154 between the first side that faces the chest of the patient 16 and the second side that faces away from the chest of the patient 16 can be between 0.2 centimeters to 5 centimeters, however, in some embodiments, the dimension can be less than 0.2 centimeters or greater than 5 centimeters. The magnetic transmitting elements can be strong enough to generate a magnetic field at a distance of between 5 and 20 centimeters. In some embodiments, the magnetic transmitting elements can be strong enough to generate a magnetic field at a distance of 13 centimeters. In some embodiments, the magnetic transmitting elements can be strong enough to generate a magnetic field along a length of line 158. As discussed herein, the magnetic field generator 154 can also include two or more magnetic coils wherein the coils are driven with opposite current polarities to increase the rapid decay of the magnetic field over a distance; thereby reducing or eliminating a magnetic field in an area of an x-ray detector, which can typically be located 5 centimeters to 20 centimeters from the chest of the patient 16 (among other ferrous objects which may distort the magnetic field within the motion box 156).

In some examples, when the mobile localized magnetic field generator 154 is placed on the chest of the patient 16, the motion box 156 can be a cylinder with a diameter of approximately 15 centimeters that begins approximately 4 centimeters away from the mobile localized magnetic field generator 154 and extends a distance (represented by line 158) of approximately 14 centimeters. As such, the motion box 156 can have a height of approximately 8 to 10 centimeters. However, such dimensions of the motion box 156 are not inclusive and the motion box 156 can have dimensions that are larger or smaller than those discussed herein. For example, in one embodiment where the localized magnetic field generator 154 is assembled onto an aperture on or over an operating room table (a non-mobile configuration), the various magnetic coils that comprise the array of magnetic coils within the localized magnetic field generator 154 may be significantly more spaced apart then in the mobile configuration. In such embodiments, the motion box 156 can be a square, cylinder, pyramidal shape, etc. (based on the positioning of the magnetic coils), and the size of the motion box can vary depending on the application. For example, where it is desirable to track a catheter from insertion within a femoral vein within the leg to a location within the patient's heart, the motion box 156 may be a meter wide, a meter long, and at least one third of a meter deep.

In further more specific embodiments, where desirable, a motion box 156 may include multiple segments that may be activated and deactivated based on an area of interest at a given time. Using the above application as an example, where it is desirable to track a catheter from insertion within a femoral vein within the leg to a location within the patient's heart; to minimize the effect of ferrous objects in proximity to the produced magnetic field, a clinician and/or magnetic field controller may deactivate segments of the magnetic field (e.g., portions of the motion box 156) where localization of a catheter is taking place in another segment of the magnetic field. As one specific example, where a catheter including magnetic sensors is being localized by the system within an area of the motion box 156 associated with the lower extremities of the patient 16, other segments of the magnetic field may be deactivated (e.g., de-powering magnetic coils in segments associated with the patient's upper extremities and chest). As the catheter moves toward another segment of the motion box, multiple segments may operate simultaneously (at least temporarily until the magnetic sensors in the catheter may be accurately located with only the magnetic coils associated with a chest cavity segment of the motion box).

Figure 11A:
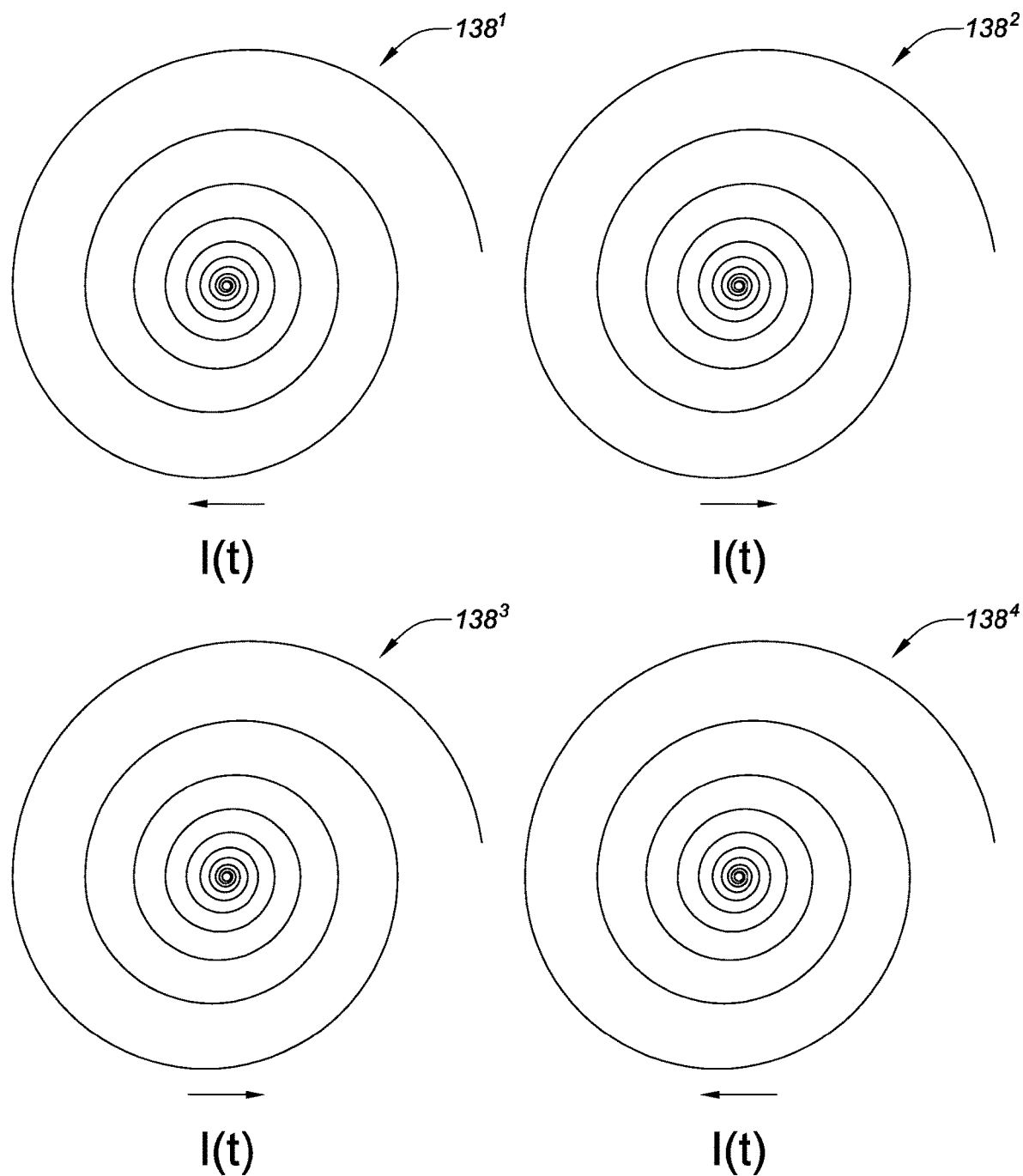
FIGS. 11A-C depict diagrammatic views of magnetic field generators for tracking of an object, consistent with various aspects of the present disclosure.
Figure 11B:
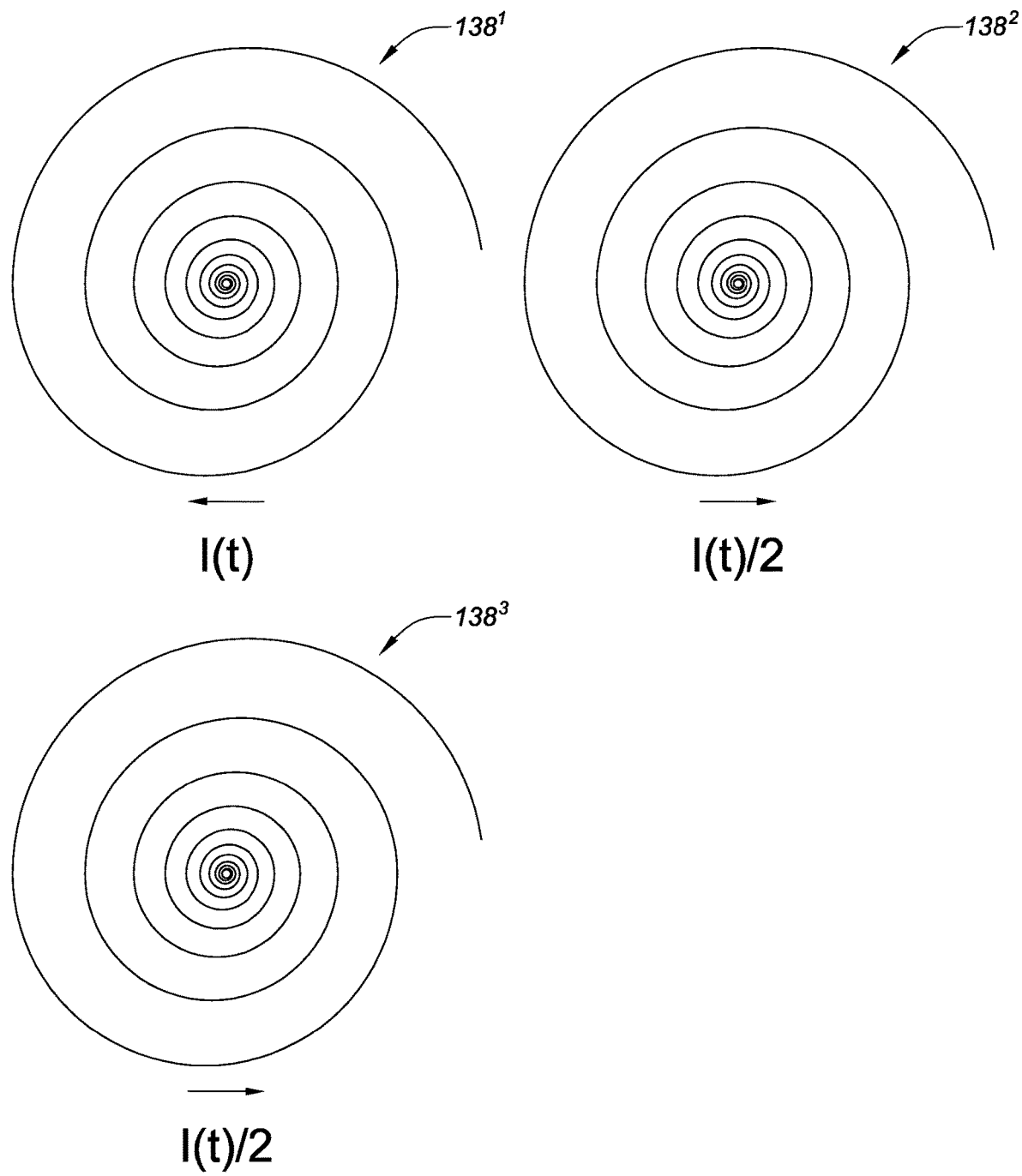
Figure 11C:
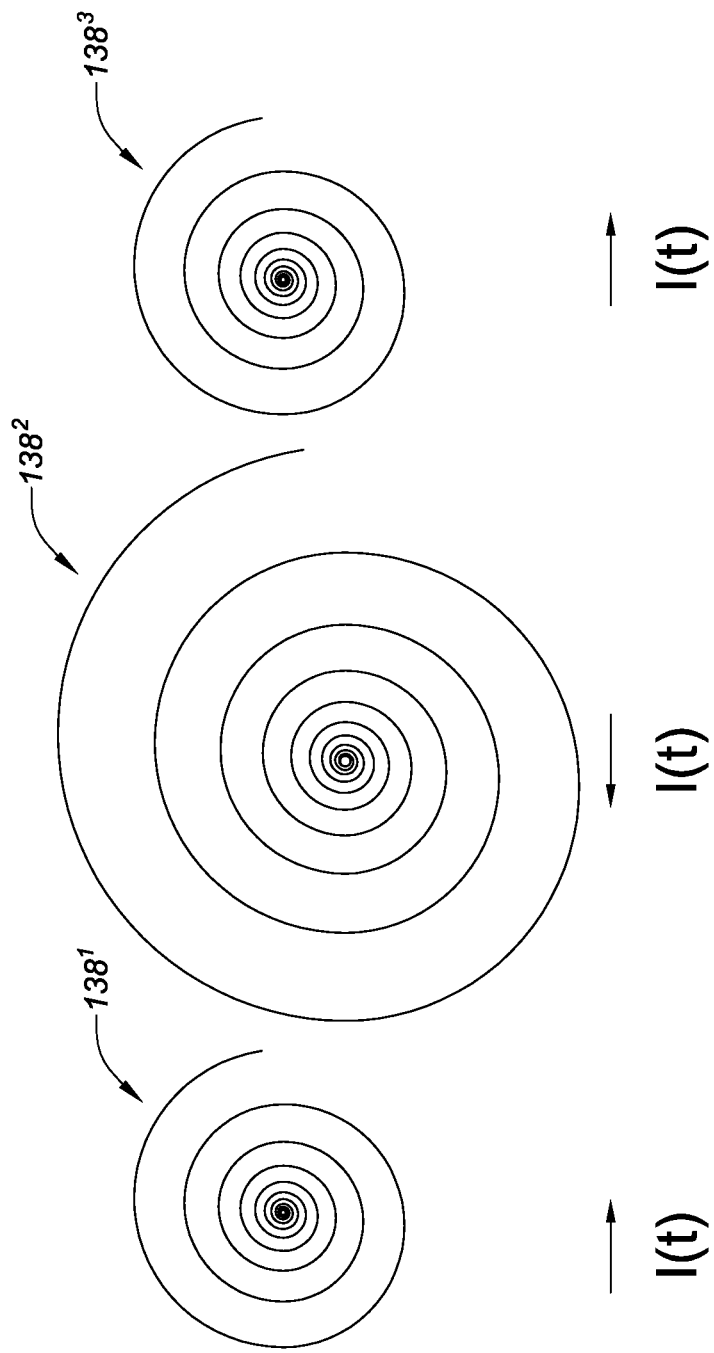

FIGS. 11A-C depict magnetic field generators for generating a magnetic field for tracking of an object within the field, consistent with various aspects of the present disclosure. To greatly increase a magnetic field decay rate, the use of four coils $138^{1-4}$ operating in an array, as shown in FIG. 11A, with one pair operating in a first polarity and a second pair operating in a second polarity produces an octupole decay rate, such as $(1/r)^{\wedge}5$ (where r is the distance from the coil). It is to be understood that various other configurations and quantities of transmitter coil arrays are considered and readily implemented in view of the present disclosure. In this way, based on a given application (or magnetic field demand), additional coils may be added to an array or alternatively more complex coils to produce higher magnetic fields, such as by adding additional windings or winding shapes with improved efficiencies. In yet other embodiments (or in combination with the above embodiments), the two or more magnetic coils of a magnetic field generator array may be driven at opposing and varying currents in order to achieve a desired magnetic field decay rate, magnetic field strength at an area of interest (e.g., motion box), direct the magnetic field toward an area of interest and/or away from a magnetic distortion object, and/or direct an orientation of magnetic field lines in the area of interest and/or near a magnetic distorting object.

As shown in FIG. 11B, an odd number of magnetic field transmitters $138^{1-3}$ can also be used in a magnetic field generator array, consistent with various aspects of the present disclosure. FIG. 11B shows a three coil array, where the coils are the same size (e.g., same number of windings, size, and length), and each coil can be driven with a varying current in such a way as to create a balanced magnetic field with expedited field decay characteristics, a desired magnetic field strength at an area of interest (e.g., motion box), direct the magnetic field toward an area of interest and/or away from a magnetic distortion object, and/or direct an orientation of magnetic field lines in the area of interest and/or near a magnetic distorting object. In the present embodiment, the magnetic field transmitters $138^{1-3}$ are driven with varying current; specifically, the total current driving both magnetic field transmitters $138^{2-3}$ is the same current driving magnetic field transmitter $138^1$, and magnetic field transmitters $138^{2-3}$ receive a current polarity opposite to that received by magnetic field transmitter $138^1$. Driving the magnetic field transmitters $138^{1-3}$ in such a way creates a similar magnetic field effect to that produced by the magnetic field generator of FIG. 7A (e.g., a fast decaying magnetic field outside an area of interest).

FIG. 11C depicts a magnetic field generator array including magnetic field transmitters $138^{1-3}$. The length/size and/or number of windings of the magnetic field transmitters $138^{1,3}$ being less than that of magnetic field transmitter $138^2$. Specifically, the size of the magnetic field transmitters $138^{1,3}$ being designed, when combined, to produce an equal and opposite magnetic field affect to that produced by magnetic field transmitter $138^2$ when all of the magnetic field transmitters are driven by the same current (but with the magnetic field transmitters $138^{1,3}$ receiving an opposite polarity to magnetic field transmitter $138^2$). When the magnetic field generator array is driven in such a fashion, the magnetic field decay rate is substantially increased to facilitate localization of a magnetic sensor within an area of interest, but to substantially reduce the magnetic field outside of the area of interest where magnetic distortion objects can influence the magnetic field lines or otherwise degrade the accuracy of the magnetic sensor localization.

Figure 12A:
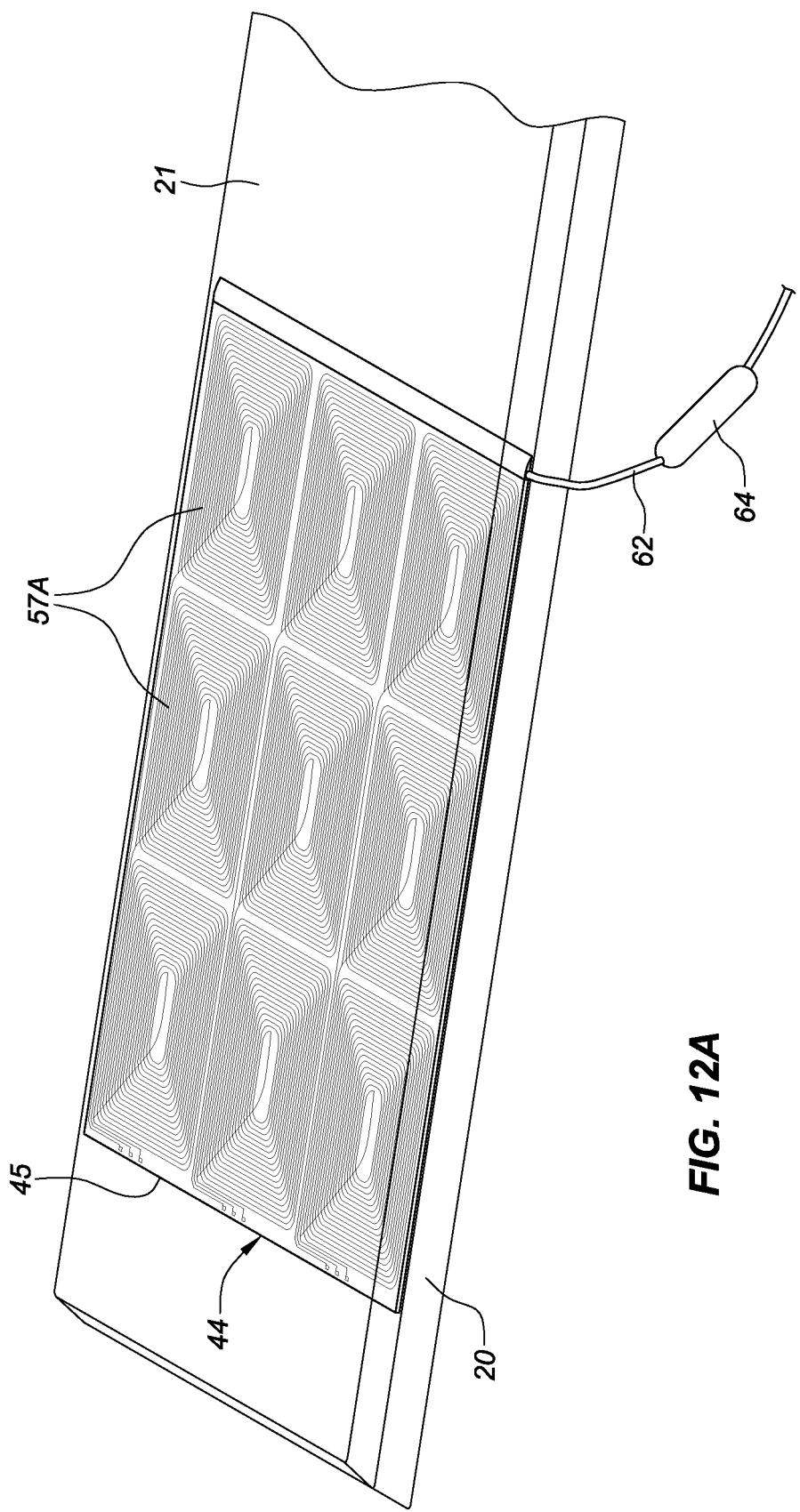
FIG. 12A is an isometric view of a magnetic field generator assembly including a matrix of a plurality of magnetic field transmitters.

Referring to FIG. 12A, magnetic field generator assembly 44 may comprise magnetic field transmitters, such as transmitters 57A, positioned within a housing 45 (or, alternatively, the transmitters may be positioned on the housing). Each transmitter 57A can comprise an elongate conductive element, such as a wire, arranged in a spiral form, such as a coil. The wire gauge used to make the spiral coils of transmitters 57A can be about 0.7 mm (width) by 1 oz. (thickness). The typical length of the wires can be about 20 meters. The separation distance between adjacent turns of the coils of transmitters 57A can be about 0.3 mm. The spiral coils of transmitters 57A can be rectangular in shape to occupy the majority of the generator assembly 44 and leave very little space unoccupied, as shown in FIG. 12A. Alternatively, transmitters may be circular in shape, as shown in FIG. 4. Regardless, in at least one embodiment, the transmitters may be thin and flat, such that they can be easily integrated into or associated with table 20. The transmitters may also be integrated into flexible circuitry. In an embodiment, the height of each transmitter can typically range from about 10 micrometers to about 0.25 millimeters. Moreover, the distance between the transmitters and the housing 45 that forms the exterior of the generator assembly 44 is minimal, ranging from about 0.2 mm to 2 cm, and the housing 45 may be about 0.2 mm to 2 cm in total height, about 10 cm to 50 cm in total width, and about 10 cm in total length. Thus, generator assembly 44 may be thin and substantially flat. As such, generator assembly 44 may be placed under a mattress or on top of an operating table 21.

Figure 12B:
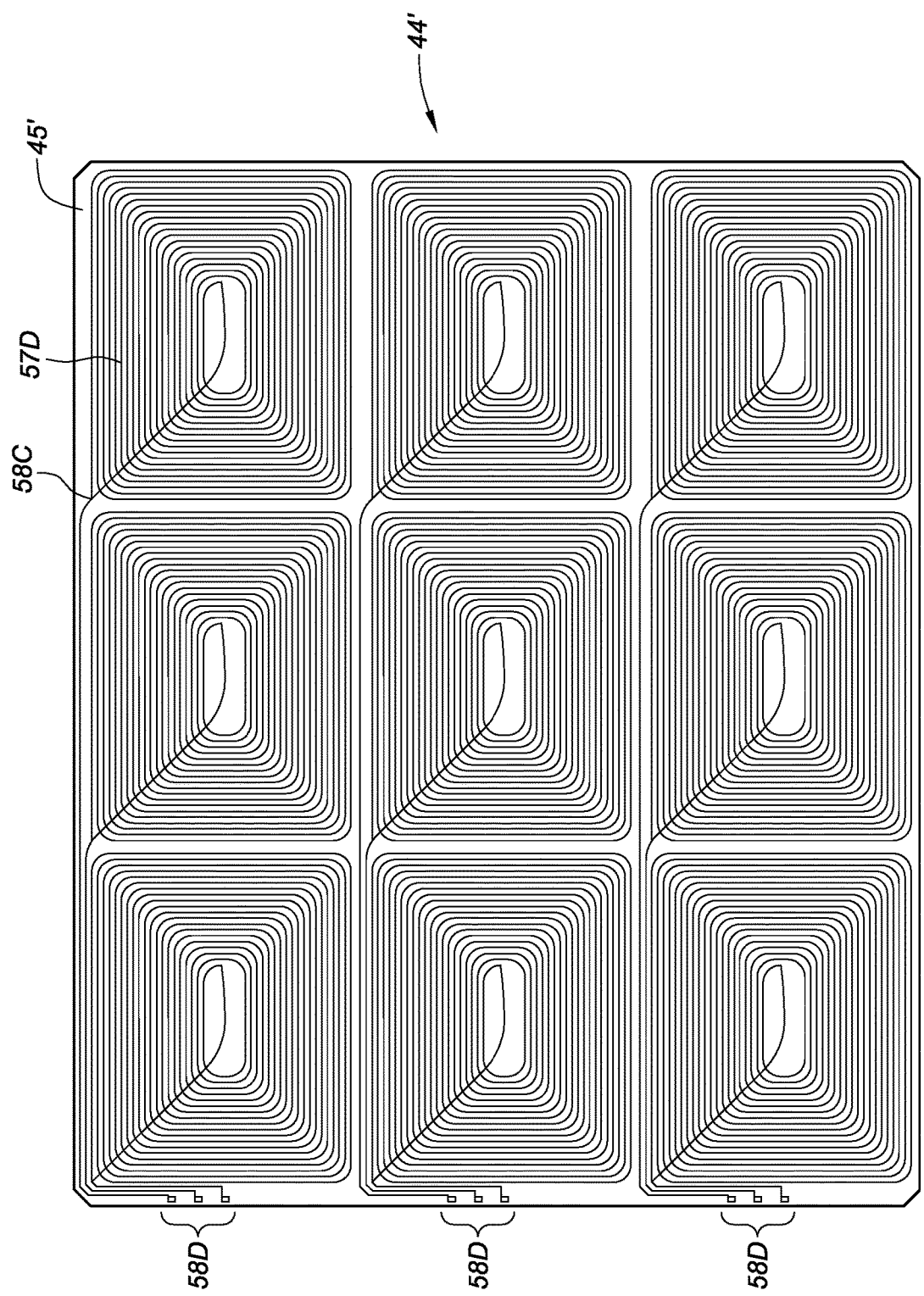
FIG. 12B is a top view of another embodiment of a magnetic field generator assembly and its wire connections.

FIG. 12B shows another embodiment of a magnetic field generator assembly 44', similar to assembly 44 shown in FIG. 12A, and coil ends 58C and 58D, which ultimately connect to a power source (not shown). In this embodiment, magnetic field transmitters 57D can be printed on a substrate or housing 45' using conductive printing ink or printed circuits, for example. The transmitters 57D can be printed on the printed circuits. Each transmitter 57D comprises a coil that begins at end 58C and ends at end 58D (or vice versa). The wiring of the transmitters 57D can be relatively thin and flat, allowing them to be transparent, or nearly transparent, to x-rays. This reduces the potential for fluoroscopic interference attributable to the transmitters 57D. Typically, at the point where coil ends 58C and 58D exit the magnetic field generator assembly 44', they lie close to one another or in a twisted pair configuration. Having only a very small distance between a wire pair and/or twisting the pair helps reduce parasitic electrical transmission from the coils, which could interfere with the magnetic field. Each of the coils in the magnetic field generator assembly 44' may be wound unidirectional (see, e.g., FIGS. 7A-B), and driven with opposite currents and/or phase offset frequencies that result in rapidly fading magnetic fields in proximity to a magnetic field distorting object.

Referring back to FIG. 12A, cable 62 provides a means for connecting assembly 44 to an ECU. Accompanying electronics 64 can be placed on and communicate with cable 62. Moreover, the electronics 64 may be used to filter electromagnetic signals going to/from transmitters and resonance circuitry, for example. Further examples of generator assemblies are disclosed in U.S. Patent Publication 2016/0287133, the entirety of which is hereby incorporated by reference as though fully set forth herein.

Figure 12C:
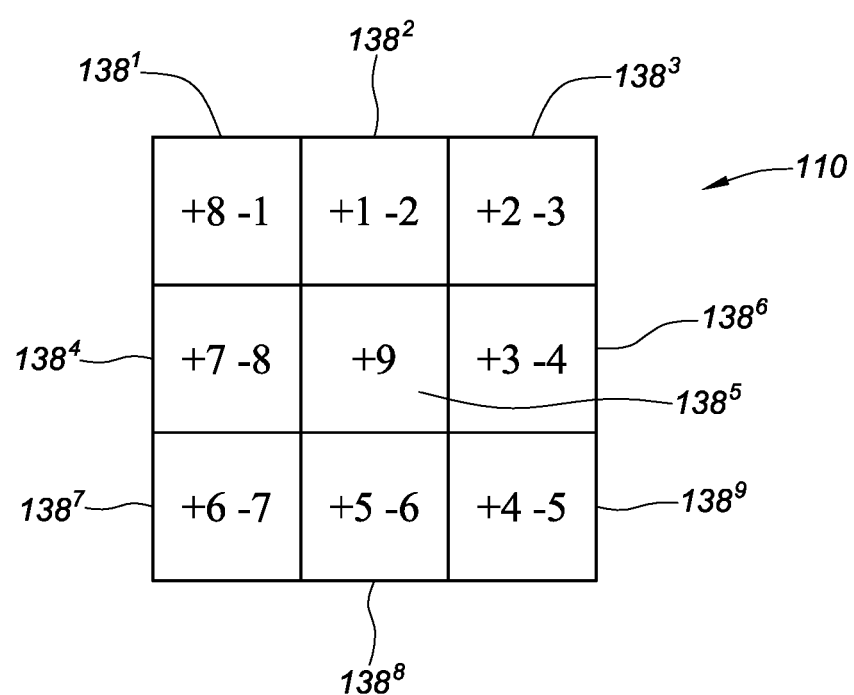
FIG. 12C is a diagrammatic view of a magnetic field generator assembly.

FIG. 12C depicts a diagrammatic view of a magnetic field generator array 110 with example transmitted frequencies of each of the magnetic field transmitters $138^{1-9}$ represented. It is to be understood that the magnetic field transmitters within the array can emit magnetic fields at varying amplitude and frequency, as well as emit multiple frequencies simultaneously (e.g., utilizing time and/or frequency based modulation). The present embodiment of the magnetic field generator array 110 includes 9 magnetic field transmitters $138^{1-9}$ positioned in a substantially rectangular fashion. As shown for example in the box indicative of magnetic field transmitter $138^1$, in the present embodiment this magnetic field transmitter is producing a magnetic field with a first signal (having a positive polarity at a frequency of 8—the numbering simply being indicative of a relative frequency for the purposes of the matrix), and a second signal (having a negative polarity at a $1^{st}$ frequency). The first signal emitted from the magnetic field transmitter $138^1$ is cancelled out by/with a second signal produced by a neighboring magnetic field transmitter $138^4$ which has an equal and opposite polarity and amplitude, and increases the magnetic field decay rate of the magnetic field created by the pair of magnetic field transmitters. Similarly, each of the neighboring magnetic field transmitters around the periphery of the array cancel out the magnetic field produced by at least one of their neighboring transmitters—creating a magnetic field around a periphery of a motion box defined by the magnetic field that exhibits an increased rate of magnetic field decay over a distance from the array. Magnetic field transmitter $138^5$ is the only transmitter that produces a magnetic field at a frequency ("+9") that is not cancelled out or otherwise affected by a field produced by a neighboring transmitter. As a result, the magnetic field generator array produces a unique magnetic field with an increased decay rate along a periphery to reduce the effect of ferrous objects in proximity to the magnetic field from introducing eddy currents into the area of interest (e.g., an area encompassed by a field produced by the magnetic field transmitter $138^5$). In such a case, the magnetic field transmitters along a periphery of the array effectively act as a buffer zone between the area of interest and ferrous objects in close proximity to the magnetic field, and/or within the buffer zone. This is due to the reduced magnetic field in the buffer zone associated with the increased magnetic field decay rate (due to the opposing magnetic field outputs of the magnetic field transmitters along the periphery of the array). The reduced magnetic field in the buffer zone reduces and/or eliminates the effect of the ferrous object's eddy current on a magnetic sensor within an area of interest of the magnetic field.

In yet other embodiments, neighboring magnetic field transmitters need not generate opposing currents for other neighboring magnetic field transmitters, but instead generate identical phase-offset signals (e.g., in an alternating current system) to cancel out neighboring magnetic transmitter coil field outputs and/or increase a magnetic field decay rate of the magnetic field generator array 110. In one specific embodiment, a plurality of magnetic field transmitting elements, arranged in a matrix, may each be driven by a unique frequency modulated signal. Two or more of the magnetic field transmitting elements may be driven by frequency modulated signals including a first frequency, but with a 180 degree phase-offset (relative to one another). The produced magnetic fields from the two or more magnetic field transmitting elements, when combined, form a rapidly fading magnetic field. This rapidly fading magnetic field may be directed toward a separate area, where a magnetic distorting object lies, for example. The rapidly fading magnetic field diminishes the effect of the magnetic distorting object on the magnetic field generated by the matrix. The unique frequency modulated signal driving each magnetic field transmitting element may produce one or more magnetic fields that when combined with the magnetic field produced by the other magnetic field transmitting elements in the array results in rapidly fading magnetic fields at a variety of frequencies.

In further more specific embodiments, controller circuitry adjusts the magnetic field by transmitting power generation signals to the signal generator for each of the two or more magnetic transmitting elements that increases a decay rate of the magnetic field to reduce the magnetic field in proximity to the magnetic distorting object.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment.

Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An apparatus for generating a desired magnetic field for tracking of an object within an area of interest, the apparatus comprising:
   a plurality of magnetic field transmitting elements that includes at least a first magnetic field transmitting element disposed on a first plane and a second magnetic field transmitting element disposed on a second plane;
   a signal generator, electrically coupled to the plurality of magnetic field transmitting elements, and configured and arranged to
   generate a first signal that drives the first magnetic field transmitting element to emit a first magnetic field,
   generate a second signal that drives the second magnetic field transmitting element to emit a second magnetic field;
   wherein the first magnetic field generated by the first magnetic field transmitting element on the first plane has an opposing polarity and/or phase to the second magnetic field generated by the second magnetic field transmitting element on the second plane,
   wherein the first magnetic field and the second magnetic field combine to generate the desired magnetic field for tracking the object in the area of interest and generates a fading magnetic field in a separate area, the area of interest located normal to the first plane and the second plane, and
   wherein the first magnetic field transmitting element and the second magnetic field transmitting element are both secured to a patient examination table,
   wherein the fading magnetic field has a decay rate of at least $(1/r)^N$, where N is four or greater and r is a distance from one of the magnetic field transmitting elements.

2. The apparatus of claim 1, wherein the plurality of magnetic field transmitting elements are located proximal to the area of interest relative to the separate area; and the magnetic fields emitted from the plurality of magnetic field transmitting elements combine to form a stronger magnetic field in proximity to the area of interest and a weaker magnetic field in proximity to the separate area.

3. The apparatus of claim 1, wherein the signal generator is further configured and arranged to adjust the fading magnetic field in the separate area by re-orientating the fading magnetic field lines to align with magnetic poles of a magnetic field-disrupting component within the separate area.

4. The apparatus of claim 1, wherein the signal generator is further configured and arranged to adjust the fading magnetic field to form a magnetic void around a magnetic field-disrupting component within the separate area.

5. The apparatus of claim 1, wherein the signal generator is further configured and arranged to drive the magnetic field transmitting elements with opposing polarities, wherein the magnetic field transmitting elements, in response to the opposing polarities, emit magnetic fields that are negated in proximity to a magnetic field-disrupting component in the separate area.

6. The apparatus of claim 1, wherein the fading magnetic field in the separate area minimizes the production of eddy currents within the separate area associated with a magnetic field-disrupting component therein.

7. The apparatus of claim 1, wherein the separate area includes a magnetic field-disrupting component, the magnetic field-disrupting component including at least one of an x-ray source associated with an x-ray imaging device, and a C-arm associated with the x-ray imaging device.

8. The apparatus of claim 1, wherein the magnetic field transmitting elements are further configured and arranged to be placed on a chest of a patient, the area of interest is a cardiac muscle, the separate area is anywhere that is in proximity to the area of interest, and the object is a cardiac catheter.

9. The apparatus of claim 1, the area of interest is a cardiac muscle, the object being tracked is a cardiac catheter, and the separate area includes ferrous objects including at least one of a C-arm, lights, surgical instruments, and an x-ray imaging device.

10. The apparatus of claim 1, wherein the signal generator, in conjunction with the magnetic field transmitting elements, are further configured and arranged to generate an asymmetric magnetic field.

11. The apparatus of claim 1, wherein the plurality of magnetic field transmitting elements are arranged in a matrix, and a first of the plurality of magnetic field transmitting elements is configured and arranged to be driven by a first frequency modulated signal including a first frequency, and a second of the plurality of magnetic field transmitting elements is configured and arranged to be driven by a second frequency modulated signal including the first frequency with a 180 degree phase-offset, the combined magnetic field generated by the first and second magnetic field transmitting elements include the fading magnetic field characteristics.

12. The apparatus of claim 1, wherein the first magnetic field transmitting element and the second magnetic field transmitting element are both disposed in a single plane parallel to a top surface of the patient examination table.

13. The apparatus of claim 1, wherein the first magnetic field transmitting element and the second magnetic field transmitting element are both disposed within a single housing.

\* \* \* \* \*